(12) United States Patent
Bierman

(10) Patent No.: US 8,246,583 B2
(45) Date of Patent: *Aug. 21, 2012

(54) ANCHORING SYSTEM FOR A MEDICAL ARTICLE

(75) Inventor: Steven F. Bierman, Del Mar, CA (US)

(73) Assignee: Venetec International, Inc., Covington, GA (US)

( * ) Notice: Subject to any disclaimer, the term of this patent is extended or adjusted under 35 U.S.C. 154(b) by 258 days.

This patent is subject to a terminal disclaimer.

(21) Appl. No.: 12/042,256

(22) Filed: Mar. 4, 2008

(65) Prior Publication Data

US 2008/0154208 A1 Jun. 26, 2008

Related U.S. Application Data

(63) Continuation of application No. 11/045,673, filed on Jan. 28, 2005, which is a continuation of application No. 10/107,546, filed on Mar. 26, 2002, now Pat. No. 6,951,550, which is a continuation of application No. 09/379,827, filed on Aug. 24, 1999, now Pat. No. 6,361,523, which is a continuation-in-part of application No. 09/049,825, filed on Mar. 27, 1998, now Pat. No. 6,283,945.

(60) Provisional application No. 60/062,323, filed on Oct. 17, 1997.

(51) Int. Cl.
 *A61M 5/32* (2006.01)
(52) U.S. Cl. ............... 604/174; 128/DIG. 26; 248/68.1; 248/65
(58) Field of Classification Search .................. 604/174, 604/178–180, 903; 128/877, DIG. 26; 248/68.1, 248/49, 65, 74.4, 74.2, 55
See application file for complete search history.

(56) References Cited

U.S. PATENT DOCUMENTS 2,525,398 A 10/1950 Collins
(Continued)

FOREIGN PATENT DOCUMENTS

CA 2 228 747 2/1997
(Continued)

OTHER PUBLICATIONS

European Search Report for application No. EP 04 07 6329, 3 pp., Feb. 7, 2005.

*Primary Examiner* — Quynh-Nhu H Vu
(74) *Attorney, Agent, or Firm* — Knobbe Martens Olson & Bear LLP

(57) ABSTRACT

An anchoring system secures a catheter to the body of a patient and arrests axial movement of the catheter without meaningfully impairing fluid flow through the catheter. The anchoring system includes an anchor pad that adheres to the patient's skin and supports a retainer. The retainer includes interacting structure with a cooperating keeper and latch that releasably moves the retainer between an open and a closed position. When in the open position, the retainer can receive a portion of the catheter and be subsequently moved to the closed position. The retainer further includes one or more retention mechanisms that inhibit axial movement of the catheter relative to the retainer when the catheter is secured therein. In one mode, the retainer includes interacting structure with a keeper and latch. The keeper selectively cooperates with the latch to secure the retainer in a closed position where the cover is generally over to the base. In another mode, the anchoring system includes a mount that allows the retainer to rotate 360° relative to the anchor pad.

25 Claims, 14 Drawing Sheets

U.S. PATENT DOCUMENTS

| | | | |
|---|---|---|---|
| 2,707,953 A | 5/1955 | Ryan | |
| 2,893,671 A | 7/1959 | Flora et al. | |
| 3,059,645 A | 10/1962 | Hasbrouck et al. | |
| 3,064,648 A | 11/1962 | Bujan | |
| 3,482,569 A | 12/1969 | Raffaelli, Sr. | |
| 3,630,195 A | 12/1971 | Santomieri | |
| 3,632,071 A | 1/1972 | Cameron et al. | |
| 3,677,250 A | 7/1972 | Thomas | |
| 3,766,915 A | 10/1973 | Rychlik | |
| 3,856,020 A | 12/1974 | Kovac | |
| 3,896,527 A | 7/1975 | Miller et al. | |
| 3,906,592 A | 9/1975 | Sakasegawa et al. | |
| 3,906,946 A | 9/1975 | Nordstrom | |
| 3,973,565 A | 8/1976 | Steer | |
| 3,993,081 A | 11/1976 | Cussell | |
| 4,020,835 A | 5/1977 | Nordstrom et al. | |
| 4,030,540 A * | 6/1977 | Roma | 165/172 |
| 4,057,066 A | 11/1977 | Taylor | |
| 4,059,105 A | 11/1977 | Cutruzzula et al. | |
| 4,129,128 A | 12/1978 | McFarlane | |
| 4,133,307 A | 1/1979 | Ness | |
| 4,149,539 A * | 4/1979 | Cianci | 606/192 |
| 4,161,177 A | 7/1979 | Fuchs | |
| 4,170,995 A | 10/1979 | Levine et al. | |
| 4,193,174 A | 3/1980 | Stephens | |
| 4,224,937 A | 9/1980 | Gordon | |
| 4,248,229 A | 2/1981 | Miller | |
| 4,250,880 A | 2/1981 | Gordon | |
| 4,316,461 A | 2/1982 | Marais et al. | |
| 4,326,519 A | 4/1982 | D'Alo et al. | |
| 4,333,468 A | 6/1982 | Geist | |
| 4,362,156 A | 12/1982 | Feller, Jr. et al. | |
| 4,392,853 A | 7/1983 | Muto | |
| 4,397,647 A | 8/1983 | Gordon | |
| 4,442,994 A * | 4/1984 | Logsdon | 248/547 |
| 4,449,975 A | 5/1984 | Perry | |
| 4,453,933 A | 6/1984 | Speaker | |
| 4,480,639 A | 11/1984 | Peterson et al. | |
| 4,517,971 A | 5/1985 | Sorbonne | |
| 4,579,120 A | 4/1986 | MacGregor | |
| 4,583,976 A | 4/1986 | Ferguson | |
| 4,659,329 A | 4/1987 | Annis | |
| 4,711,636 A | 12/1987 | Bierman | |
| 4,726,716 A | 2/1988 | McGuire | |
| 4,742,824 A | 5/1988 | Payton et al. | |
| 4,808,162 A | 2/1989 | Oliver | |
| 4,838,878 A | 6/1989 | Kalt et al. | |
| 4,852,844 A | 8/1989 | Villaveces | |
| 4,857,058 A | 8/1989 | Payton | |
| 4,863,432 A | 9/1989 | Kvalo | |
| 4,897,082 A | 1/1990 | Erskine | |
| 4,898,587 A | 2/1990 | Mera | |
| 4,899,963 A | 2/1990 | Murphy | |
| 4,919,654 A | 4/1990 | Kalt | |
| 4,932,943 A | 6/1990 | Nowack | |
| 4,955,864 A | 9/1990 | Hajduch | |
| 4,976,700 A | 12/1990 | Tollini | |
| 5,037,397 A | 8/1991 | Kalt et al. | |
| 5,073,170 A | 12/1991 | Schneider | |
| 5,084,026 A | 1/1992 | Shapiro | |
| 5,098,399 A | 3/1992 | Tollini | |
| 5,100,393 A | 3/1992 | Johnson | |
| 5,147,322 A | 9/1992 | Bowen et al. | |
| 5,156,641 A | 10/1992 | White | |
| 5,188,609 A | 2/1993 | Bayless et al. | |
| 5,192,273 A | 3/1993 | Bierman et al. | |
| 5,192,274 A | 3/1993 | Bierman | |
| 5,195,981 A | 3/1993 | Johnson | |
| 5,226,892 A | 7/1993 | Boswell | |
| 5,234,185 A * | 8/1993 | Hoffman et al. | 248/56 |
| 5,266,401 A | 11/1993 | Tollini | |
| 5,292,312 A | 3/1994 | Delk et al. | |
| 5,304,146 A | 4/1994 | Johnson et al. | |
| 5,306,243 A | 4/1994 | Bonaldo | |
| 5,314,411 A | 5/1994 | Bierman | |
| 5,334,186 A * | 8/1994 | Alexander | 604/180 |
| 5,338,308 A | 8/1994 | Wilk | |
| 5,342,317 A | 8/1994 | Claywell | |
| 5,344,406 A | 9/1994 | Spooner | |
| 5,354,282 A | 10/1994 | Bierman | |
| 5,368,575 A | 11/1994 | Chang | |
| 5,380,293 A | 1/1995 | Grant | |
| 5,389,082 A | 2/1995 | Baugues et al. | |
| 5,398,679 A | 3/1995 | Freed | |
| 5,403,285 A | 4/1995 | Roberts | |
| 5,413,562 A | 5/1995 | Swauger | |
| 5,443,460 A | 8/1995 | Miklusek | |
| 5,456,671 A | 10/1995 | Bierman | |
| 5,468,231 A | 11/1995 | Newman et al. | |
| 5,470,321 A | 11/1995 | Forster et al. | |
| D364,922 S | 12/1995 | Bierman | |
| 5,496,282 A | 3/1996 | Militzer et al. | |
| 5,496,283 A | 3/1996 | Alexander | |
| 5,499,976 A | 3/1996 | Dalton | |
| 5,520,656 A | 5/1996 | Byrd | |
| 5,527,293 A | 6/1996 | Zamierowski | |
| D375,355 S | 11/1996 | Bierman | |
| 5,626,565 A | 5/1997 | Landis et al. | |
| 5,632,274 A * | 5/1997 | Quedens et al. | 600/394 |
| 5,672,159 A | 9/1997 | Warrick | |
| 5,681,290 A | 10/1997 | Alexander | |
| 5,685,859 A | 11/1997 | Kornerup | |
| 5,690,617 A | 11/1997 | Wright | |
| 5,916,199 A * | 6/1999 | Miles | 604/174 |
| 5,944,696 A * | 8/1999 | Bayless et al. | 604/174 |
| 6,001,081 A * | 12/1999 | Collen | 604/174 |
| 6,074,368 A | 6/2000 | Wright | |
| 6,113,577 A | 9/2000 | Hakky et al. | |
| 6,283,945 B1 | 9/2001 | Bierman | |
| 6,361,523 B1 | 3/2002 | Bierman | |
| 6,413,240 B1 | 7/2002 | Bierman et al. | |
| 6,428,514 B1 | 8/2002 | Goebel et al. | |
| 6,458,104 B2 | 10/2002 | Gautsche | |
| 6,500,154 B1 | 12/2002 | Hakky et al. | |
| 6,663,600 B2 | 12/2003 | Bierman et al. | |
| 6,951,550 B2 | 10/2005 | Bierman | |
| 7,018,362 B2 | 3/2006 | Bierman et al. | |
| 2002/0120224 A1* | 8/2002 | Zia et al. | 604/6.16 |
| 2005/0192539 A1 | 9/2005 | Bierman et al. | |
| 2006/0129103 A1 | 6/2006 | Bierman et al. | |
| 2006/0135944 A1* | 6/2006 | Bierman | 604/500 |
| 2006/0233652 A1 | 10/2006 | Kim et al. | |
| 2007/0142782 A2* | 6/2007 | Bierman | 604/174 |
| 2007/0276335 A1* | 11/2007 | Bierman | 604/180 |

FOREIGN PATENT DOCUMENTS

| | | |
|---|---|---|
| CA | 2 208 577 | 5/1997 |
| CA | 2 306 802 | 4/1999 |
| CA | 2 310 030 | 5/1999 |
| CA | 2 402 507 | 9/2001 |
| CA | 2 418 000 | 2/2002 |
| CA | 2 483 995 | 2/2002 |
| EP | 0064284 A2 | 11/1982 |
| EP | 356683 A | 3/1990 |
| EP | 0440 101 A2 | 8/1991 |
| EP | 0 931 560 | 7/1999 |
| FR | 2381529 | 9/1978 |
| GB | 2219034 | 11/1989 |
| GB | 2288542 A | 10/1995 |
| JP | S60-051377 | 4/1985 |
| JP | H04-037448 | 3/1992 |
| JP | H08-257138 | 10/1996 |
| WO | WO 92/19309 | 7/1992 |
| WO | WO 96/26756 | 9/1996 |

* cited by examiner

ANCHORING SYSTEM FOR A MEDICAL ARTICLE

RELATED CASES

This application is a continuation of co-pending U.S. application Ser. No. 11/045,673, filed Jan. 28, 2005, which is a continuation of Ser. No. 10/107,546, filed Mar. 26, 2002, which issued as U.S. Pat. No. 6,951,550, which is a continuation of U.S. application Ser. No. 09/379,827, filed Aug. 24, 1999, which issued as U.S. Pat. No. 6,361,523, which is a continuation-in-part of U.S. application Ser. No. 09/049,825, filed Mar. 27, 1998, which issued as U.S. Pat. No. 6,283,945, which claims the benefit of provisional Application No. 60/062,323, filed Oct. 17, 1997, each of which is hereby incorporated herein by reference in its entirety.

BACKGROUND OF THE INVENTION

1. Field on the Invention

The present invention relates to an anchoring system for securing a medical article to a patient to inhibit movement or migration of the medical article relative to the patient.

2. Description of Related Art

Hospitalized patients often have limited mobility due either to their condition or to doctor's orders. Such patients must lie in bed and not move about their hospital room, even to urinate. As such, a Foley catheter is often used with the bed-confined patient to drain urine from the patient's bladder. Use of a Foley catheter thus eliminates toilet trips as well as reduces bedpan use.

A Foley catheter typically includes two coaxial lumens: a drainage lumen and an inflation lumen. The inflation lumen communicates with an inflation balloon located at the tip of the catheter (i.e., the catheter proximal end). The proximal end of the drainage lumen includes one or more influent openings to receive urine from the bladder. The lumens usually diverge in a Y-type pattern at the distal end of the catheter to form an effluent port and an inflation port.

In use, a healthcare provider inserts the Foley catheter through the urinary tract of the patient to locate the tip of the catheter within the patient's bladder. Although the catheter usually includes a siliconized outer coating as provided by the manufacturer, healthcare providers often apply further lubricant, such as, for example, water-based jelly. The provider then inflates the balloon by attaching the inflation port to a source of pressurized working fluid (e.g., saline solution). Once inflated, a valve, which is located at the inflation port, inhibits the flow of fluid from the inflation lumen and the balloon to keep the balloon inflated. The inflated balloon prevents the catheter from unintentionally dislodging from the bladder. The healthcare provider then connects the distal end of the drainage lumen (i.e., its effluent port) to a drainage tube leading to a collection container.

The healthcare provider usually secures the distal end of the Foley catheter to the patient using tape. The healthcare provider commonly places long pieces of tape across the distal end of the catheter in a crisscross pattern to secure the catheter distal end to the inner thigh of the patient. This securement inhibits disconnection between the catheter and the drainage tube, as well as prevents the catheter or drainage tube from snagging on the bed rail or other objects.

Taped connections, however, often collect contaminates and dirt. Normal protocol therefore requires periodic tape changes in order to inhibit bacteria and germ growth at the securement site. Frequent tape changes though lead to another problem: excoriation of the patient's skin. In addition, valuable time is spent applying and reapplying the tape to secure the catheter. And healthcare providers often remove their gloves when taping because most find the taping procedure difficult and cumbersome when wearing gloves. Not only does this further lengthen the procedure, but it also subjects the healthcare provider to possible infection.

A number of catheter securement devices have been developed to obviate the need for frequent application of tape. U.S. Pat. Nos. 5,304,146 and 5,342,317 disclose several examples of such devices. Although these devices hold the catheter to the patient, they fail to arrest longitudinal movement of the catheter. These devices rely upon friction between the catheter and a band wrapped over the catheter to prevent axial movement. Such contact between the catheter and the securement device, however, often fails to arrest longitudinal (i.e., axial) movement of the catheter, especially when used with a lubricated catheter (e.g., a Foley catheter).

Other securement devices have attempted to improve the securement of Foley catheters. One such securement device is disclosed in U.S. Pat. No. 4,397,647. The approach taught by this patent, however, at least partially occludes the catheter and prevents the free flow of urine through the catheter. Improper drainage of the bladder consequently can occur, leading to patient discomfort and possible medical complications (e.g., infection).

A need therefore exists for a simply-structured anchoring system that secures a catheter to a patient, without occluding or otherwise restricting fluid flow through the catheter.

SUMMARY OF THE INVENTION

One aspect of the present invention thus involves an anchoring system for securing a medical article to the body of a patient. The system comprises an anchor pad having an upper surface and a lower surface. The lower surface has an adhesive layer which adheres to the body of a patient. A retainer is mounted onto the upper surface of the anchor pad and receives a portion of the medical article. The retainer is formed by a base and a cover. The base has a first side and a second, opposite side. The base also includes a groove having a curvilinear cross-sectional shape. The cover is formed in a similar manner as the base. The first side of the cover attaches to the first side of the base and the second side of the cover is moveable between a closed position, in which the second side of the cover lies generally above the second side of the base, and an open position, in which the second side of the cover is spaced apart from the second side of the base so as to expose the groove in the base. When the cover is closed, the grooves in the base and cover define a channel having a curvilinear cross-sectional shape. The cross-sectional area of the channel varies over the length of the channel. Also, a latching mechanism, which is operable between the base and the cover, releasably secures the second side of the cover to the second side of the base.

Another aspect of the present invention involves an anchoring system including an anchor pad with an upper surface and a lower surface. At least a portion of the lower surface is formed with an adhesive layer for attachment to the patient's skin. A retainer is permanently affixed to the upper surface of the anchor pad and comprises a base and a cover. The base has a first groove to receive at least a portion of an elongated medical article. The cover is pivotally coupled to the base and moveable between an open position and a closed position. In the open position, the groove is exposed, and in the closed position, the groove is covered. The cover also includes a second groove that cooperates with the first groove when the cover is in the closed position to define a channel. The channel is configured to support the portion of the medical article received by the retainer on at least diametrically opposed sides thereof along the entire length of the received portion of the medical article. At least one retention member projects into the channel and is arranged to engage a portion of the medical article to inhibit longitudinal movement of the medical article through the channel. Interengaging structure also cooperates between the base and cover to releasably secure the cover to the base.

In accordance with an additional aspect of the present invention, the anchoring system comprises an anchor pad with upper and lower surfaces. At least a portion of the lower surface is formed by an adhesive layer. A retainer is affixed to the upper surface of the anchor pad and comprises a base and a cover. The base has a first groove to receive at least a portion of the elongated medical article. The cover is pivotally coupled to the base and is moveable between an open position and a closed position. The cover also includes a second groove that cooperates with the first groove when the cover is in the closed position to define a channel. The channel is configured to accept a portion of the medical article received by the base. The base and cover include interengaging structure which releasably secures together the base and the cover in the closed position. At least one retention mechanism is positioned within the channel and includes at least first and second members that are arranged to cooperate with one another when the cover is closed to hold a structural portion of the medical article between the first and second members without substantially occluding the inner lumen of the medical article.

Another aspect of the present invention involves an anchoring system for securing an elongated medical article to the skin of a patient. The anchoring system includes a retainer comprising a base and a cover. The cover is pivotally coupled to the base and is movable between an open position and a closed position. A latching mechanism operates between the base and the cover to selectively secure the cover to the base when the cover is in the closed position. The latching mechanism has an operator attached to either the cover or the base, and is depressible from a locked position to an unlocked position. The latching mechanism secures the cover to the base with the operator in the locked position. The latching mechanism also permits movement of the cover relative to the base with the operator in the unlocked position.

In one mode, the latching mechanism includes a set of interengaging members that engage together with the cover in the closed position. The operator is connected to at least one of the interengaging members to disengage the interengaging members when the operator is depressed into the unlocked position. In a preferred form, the interengaging members comprise a keeper and a latch that receives the keeper in the locked position. The operator is connected to the latch. Both the keeper and the latch include tangs that interlock when the operator is in the locked position and the cover is in the closed position. The keeper includes a deflectable bar that is attached to and extends from either the base or the cover and supports one of the interlocking tangs. The latch includes an actuating bar. The actuating bar is attached to and extends from either the base of the cover and supports the other interlocking tang. The operator is connected to the actuating bar such that when the operator is depressed, the actuator bar bends to thereby disengage the respective tang from the tang of the keeper. In one variation, the operator includes a channel in which the tang of the latch is disposed. The channel is sized to receive at least a portion of the keeper. This latching mechanism presents a simply structured mechanism that is easily actuated to lock and unlock the cover from the base.

Another aspect of the present invention involves an anchoring system including an anchor pad having an upper surface and a lower surface. At least a portion of the lower surface is formed with an adhesive. A retainer is rotatably attached to the upper surface of the anchor pad. The retainer includes a base and a cover, with the cover being pivotally coupled to the base. The cover is movable between an open position and a closed position. The cover and the base cooperate to define a channel when the cover lies in the closed position. The channel is configured to receive at least a portion of the elongated medical article. At least one retention member projects into the channel is arranged so as to be capable of engaging a portion of the medical article and inhibiting axial movement of the medical article through the channel. A latching mechanism operates between the base and the cover of the retainer selectively secure the cover to the base when the cover is in the closed position. The pivotal movement of the retainer relative to the anchor pad allows the orientation of the medical article retained by the anchor system to change so as to ease connection and disconnection of the medical article from the anchoring system, as well as for aligning the retained medical article with associated medical components.

Further aspects, features and advantages of the present invention will become apparent from the detailed description of the preferred embodiments that follows.

BRIEF DESCRIPTION OF THE DRAWINGS

The above mentioned and other features of the invention will now be described with reference to the drawings of preferred embodiments of the present anchoring system. The illustrated embodiments of the anchoring system are intended to illustrate, but not to limit the invention. The drawings contain the following figures.

DETAILED DESCRIPTION OF PREFERRED EMBODIMENTS OF THE INVENTION

Figure 1:
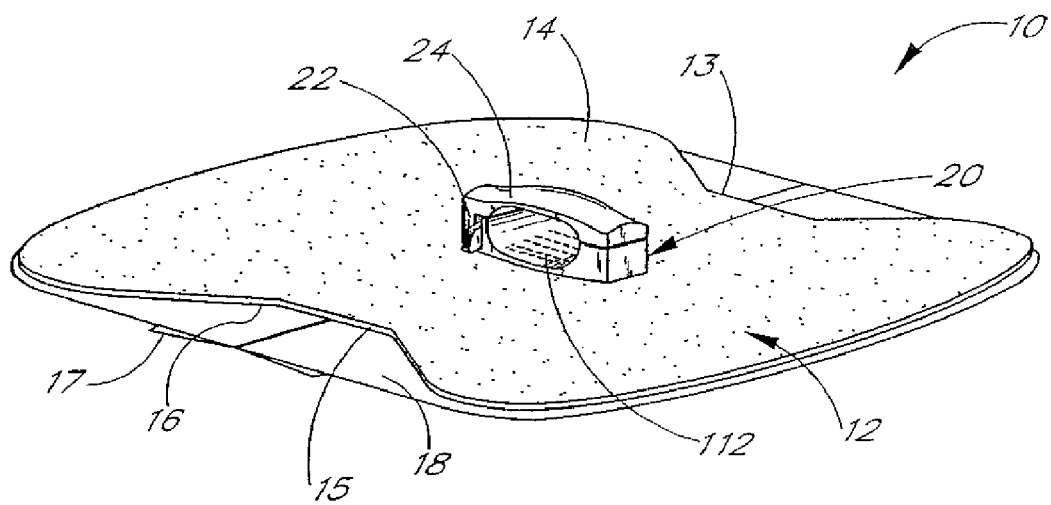
FIG. 1 is a perspective view of an anchoring system in accordance with a preferred embodiment of the present invention and illustrates the anchoring system from a proximal end.

The present embodiment of the medical article anchoring system is disclosed in the context of an exemplary Foley type catheter. The principles of the present invention, however, are not limited to Foley catheters. Instead, it will be understood by one of skill in this art, in light of the present disclosure, that the anchoring system and retainer disclosed herein also can be successfully utilized in connection with other types of medical articles, including other types of catheters, fluid drainage and delivery tubes and electrical wires. For example, but without limitation, the retainer disclosed herein can also be configured to receive and secure central venous catheters, peripherally inserted central catheters, hemodialysis catheters, surgical drainage tubes, feeding tubes, chest tubes, nasogastric tubes, scopes, as well as electrical wires or cables connected to external or implanted electronic devices or sensors. One skilled in the art can also find additional applications for the devices and systems disclosed herein. Thus, the illustration and description of the anchoring system in connection with a Foley catheter is merely exemplary of one possible application of the anchoring system.

The anchoring system described herein is especially adapted to arrest axial movement of the catheter with a slippery coating, as well as hold the catheter against the patient. For this purpose, the anchoring system 10 utilizes one or more retention mechanisms. The anchoring system accomplishes this though without meaningfully impairing (i.e., substantially occluding) the fluid flow through the catheter to a degree that would create complications. As described below, such retention mechanisms involve, among others, the shape of the channel that retains a section of the catheter, retaining structure either aligned with or positioned within the channel, a securement barb(s) and/or friction ridge(s) that bites into the catheter body without substantially occluding the catheter drainage lumen, and/or cooperating members that come together to clamp onto or pin a portion of the catheter (e.g., a webbing formed between the branches at the Foley catheter Y-site).

The anchoring system also desirably releasably engages the catheter. This allows the catheter to be disconnected from the anchoring system, and from the patient, for any of a variety of known purposes. For instance, the healthcare provider can want to remove the catheter from the anchoring system to ease disconnection of the catheter from the drainage tube or to clean the patient. The disengagement of the catheter from the anchoring system, however, can be accomplished without removing the anchoring system from the patient.

Before describing the present anchoring system in detail, a brief description of a Foley catheter is provided to assist the reader's understanding of the exemplary embodiment that follows. As best understood from FIG. 6, the catheter 8 includes a proximal tip with an inflatable balloon (not shown) and a distal end 110. The distal end 110 includes a Y-site 112 formed by an inflation branch 114 and a drainage branch 116. The drainage branch 116 and the inflation branch 114 merge together at the Y-site 112. The lumens of these branches assume either a coaxial or side-by-side arrangement on the proximal side of the Y-site 112 to form a main catheter body 118. On the distal side of the Y-site 112, a webbing 120 extends between the two branches 114, 116 at a point next to the Y-site 112.

Figure 2:
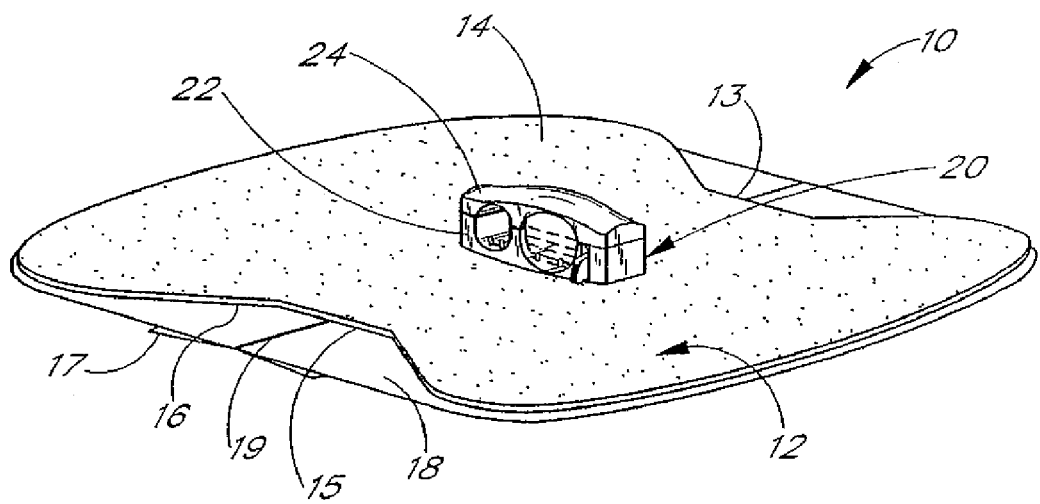
FIG. 2 is a perspective view of the anchoring system of FIG. 1 from a distal end.
Figure 3:
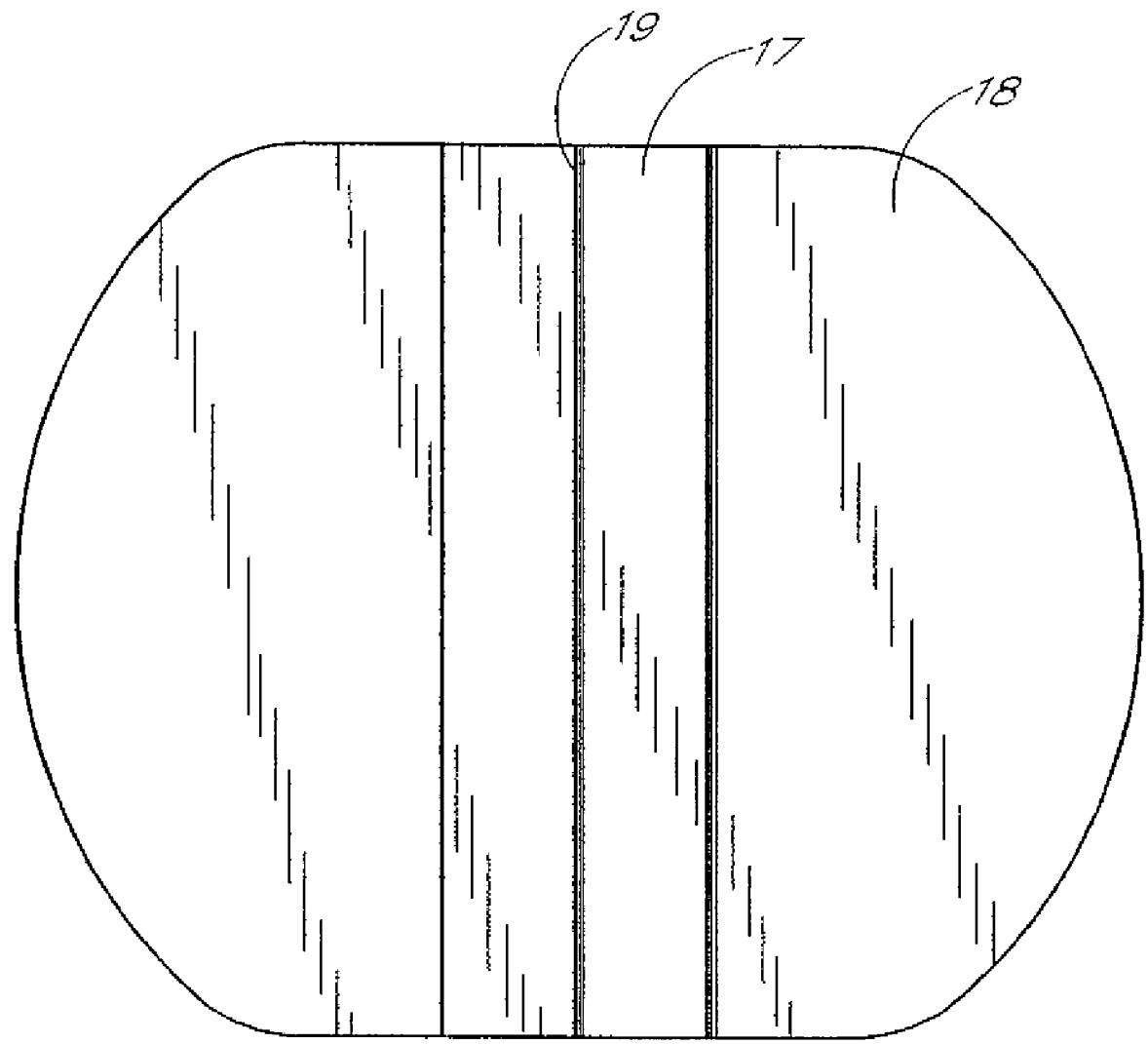
FIG. 3 is a bottom view of the anchoring system of FIG. 1.

With reference now to FIGS. 1 to 3, the anchoring system 10 includes an anchor pad 12 and a retainer 20. The anchor pad 12 secures the retainer 20 to a patient's skin. The anchor pad 12 has a lower adhesive surface 16 which adheres to the skin of a patient and a roughened upper surface 14 which supports a retainer 20. The retainer 20 is configured to accept and retain a section of a Foley catheter 8 within the anchoring system 10. In the illustrated embodiment, the retainer comprises a base 22 and a cover 24. The cover 24 is detachably secured to the base 22 and moveable between open and closed positions.

To assist in the description of these components of the anchoring system 10, the following coordinate terms are used. A "longitudinal axis" is generally parallel to the section of the catheter 8 retained by the anchoring system 10. A "lateral axis" is normal to the longitudinal axis and is generally parallel to the plane of the anchor pad 12. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. Also, the terms "proximal" and "distal", which are used to describe the present anchoring system 10, are used consistently with the description of the exemplary application. Thus, proximal and distal are used in reference to the center of the patient's body. A detailed description of the anchoring system 10, and its associated method of use, now follows.

FIGS. 1 to 3 illustrate an anchor pad 12 which desirably comprises a laminate structure with an upper foam layer (e.g., closed-cell polyethylene foam), and a lower adhesive layer. The lower adhesive layer constitutes the lower surface 16 of the anchor pad 12. The lower surface 16 desirably is a medical-grade adhesive and can be either diaphoretic or nondiaphoretic, depending upon the particular application. Such foam with an adhesive layer is available commercially from Avery Dennison of Painsville, Ohio. Although not illustrated, it will be understood that the anchor pad 12 can include suture holes in addition to the adhesive layer to further secure the anchor pad 12 to the patient's skin.

A surface of the upper foam layer constitutes an upper surface 14 of the anchor pad 12. The upper surface 14 can be roughened by corona-treating the foam with a low electric charge. The roughened or porous upper surface 14 can improve the quality of the adhesive joint (which is described below) between the base 22 and the anchor pad 12. In the alternative, the flexible anchor pad 12 can comprise a medical-grade adhesive lower layer, an inner foam layer and an upper paper or other woven or nonwoven cloth layer.

A removable paper or plastic release liner 18 desirably covers the adhesive lower surface 16 before use. The liner 18 preferably resists tearing and desirably is divided into a plurality of pieces to ease attachment of the pad to a patients skin. In the illustrated embodiment, the liner 18 is split along a center line 19 of the flexible anchor pad 12 in order to expose only half of the adhesive lower surface 16 at one time.

The liner 18 length, as measured in the lateral direction, extends beyond the center line 19 of the anchor pad 12 and is folded over, or back onto the liner 18. This folded over portion defines a pull tab 17 to facilitate removal of the liner 18 from the adhesive lower surface 16. A medical attendant uses the pull tab 17 by grasping and pulling on it so that the liner 18 is separated from the lower surface 16. The pull tab 17 overcomes any requirement that the medical attendant pick at a corner edge or other segment of the liner 18 in order to separate the liner 18 from the adhesive layer. The pull tab 17 of course can be designed in a variety of configurations. For example, the pull tab 17 can need not be located along a center line 19 of the anchor pad 12; rather, the pull tab 17 can be located along any line of the anchor pad 12 in order to ease the application of the anchor pad 12 onto the patient's skin at a specific site. For example, an area of a patient's skin with an abrupt bend, such as at a joint can require that the pull tab 17 be aligned toward one of the lateral ends of the anchor pad 12 rather than along the center line 19.

In the illustrated embodiment, the anchor pad 12 also desirably includes a pair of opposing concave sections 13, 15 that narrows the center of the anchor pad 12 proximate to the base 22. As a result, the lateral sides of the anchor pad 12 have more contact area which provides greater stability and adhesion to a patient's skin.

With reference now to FIGS. 4-10, the retainer 20 includes a rigid structure principally formed by the base 22 and the cover 24. In the illustrated embodiment, the base 22 and cover 24 are integrally formed to comprise a unitary retainer 20. This can be accomplished in any of a variety of ways well known to those skilled in the art. For instance, the entire retainer 20 can be injection molded in order to reduce fabrication costs.

Additionally, as will be apparent from the below description, several features of the retainer (e.g., a latch keeper and a hinge) desirably are flexible. Suitable ridged but flexible materials include, for example, but without limitation, plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. The illustrated retainer 20 preferably is formed by injection molded using polyethylene or polypropylene material. However, other materials can be utilized, and the retainer 20 can comprise a non-unitary base 22 and cover 24.

Figure 4:
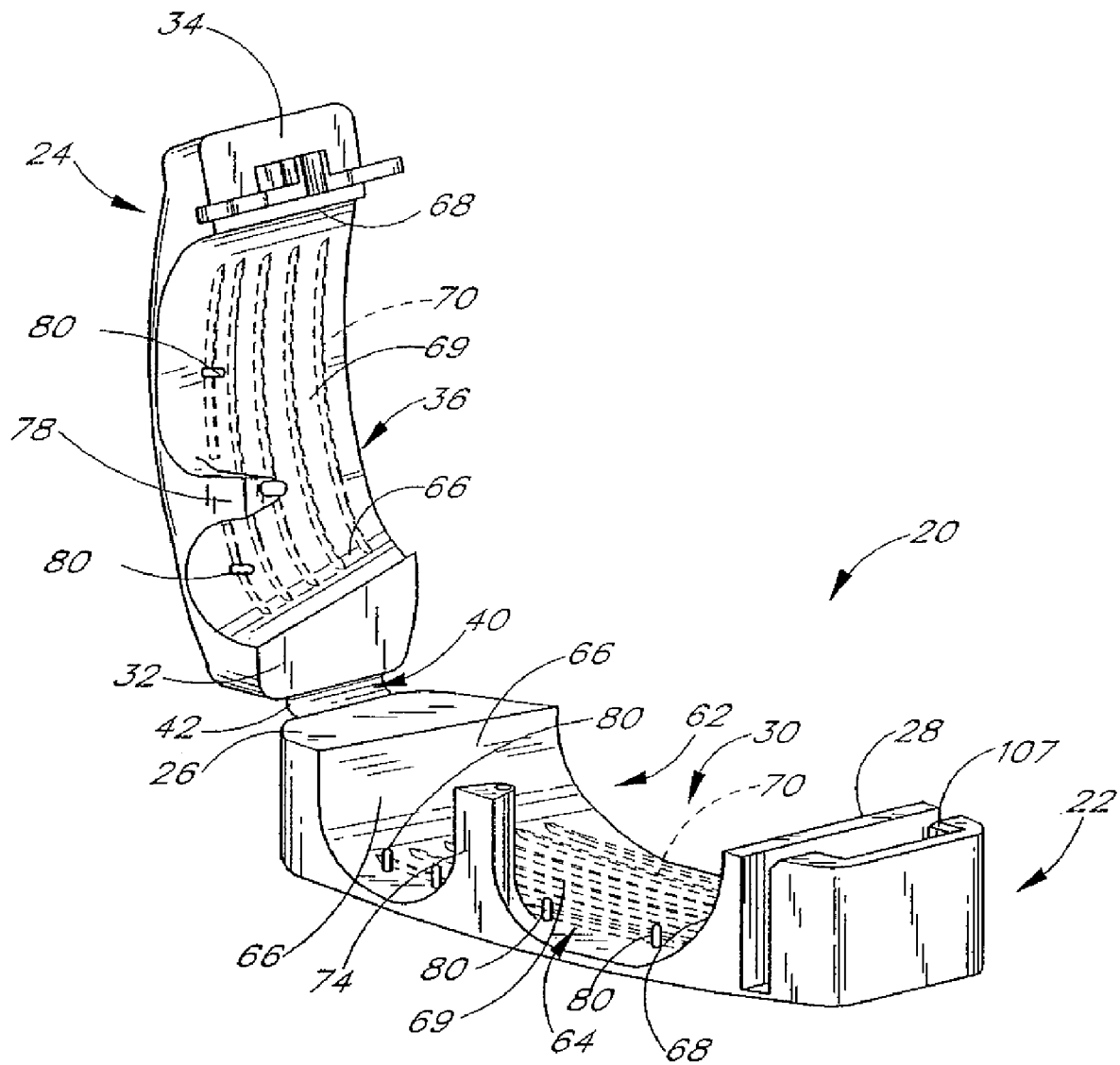
FIG. 4 is an enlarged perspective view of a retainer of the anchoring system of FIG. 2 with a cover of the retainer in an open position.

With reference to FIG. 4, a base 22 in the illustrated embodiment comprises an elongated body of a generally parallelepiped shape. The base 22, however, can be configured in a wide variety of shapes as well, such as circular, square, triangular or the like in order to suit a particular application. The longitudinal dimension of the base 22 though desirably is sufficiently long to provide stability to the catheter 8 along its length. That is, the longitudinal length of the retained catheter portion is sufficient to inhibit rocking of the catheter 8 relative to the retainer 20 (i.e., to prevent the retainer 20 from acting as a fulcrum for the catheter). Also, the lateral dimension of the base 22 desirably allows the healthcare provider to easily and naturally grip the base 22, as well as provides space on which to locate a hinge 40 and a portion of the latch mechanism 80.

The base 22 includes first and second sides 26, 28. The first side 26 lies generally at one lateral end of the base 22, and the second side 28 lies at an opposite lateral end of the base 22.

Figure 6:
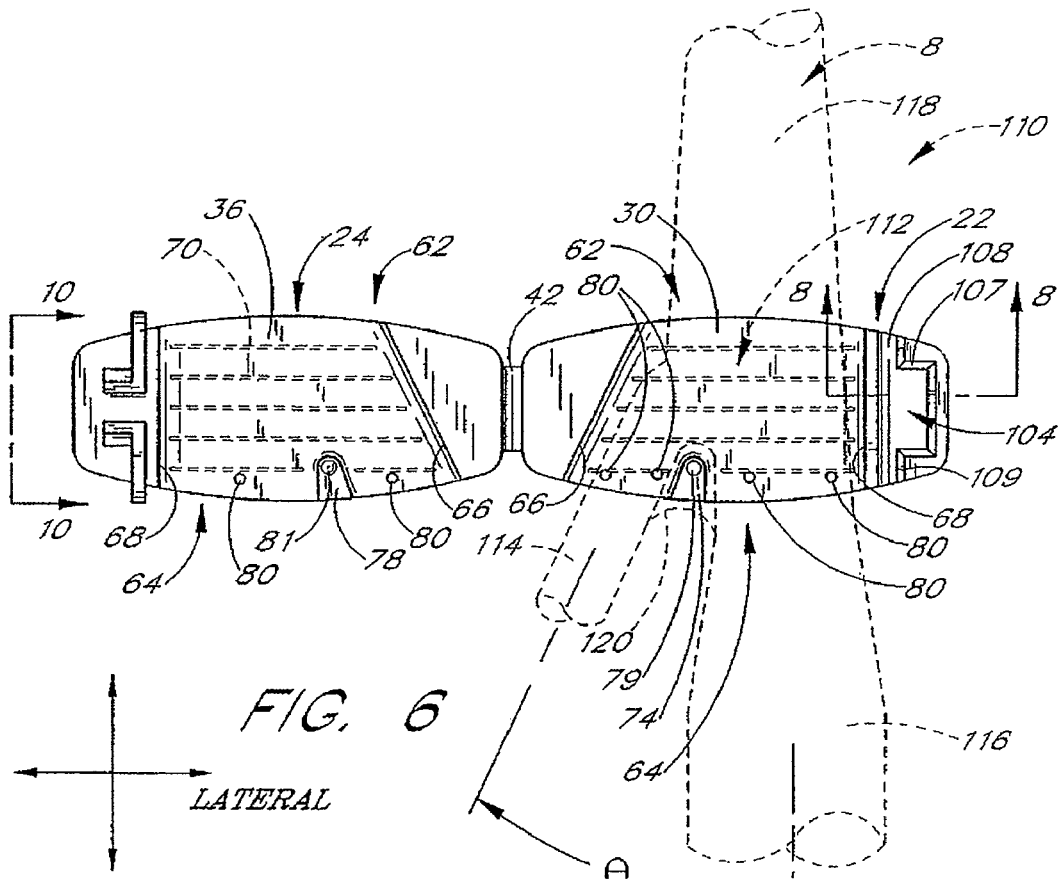
FIG. 6 is a top plan view of the retainer of FIG. 4 with the cover in a fully open position.

A groove 30 is formed on the base 22 between the first side 26 and the second side 28. In the illustrated embodiment, the groove 30 has generally a curvilinear cross-sectional shape. As best seen in FIG. 6, the lower groove 30 is also varied in width (i.e., in the lateral direction) along its longitudinal length. That is, in the illustrated embodiment, the side walls of the lower groove 30 diverge from each other in a generally linear manner from one longitudinal side of the retainer 20 to the other longitudinal side of the retainer.

The base 22 of the retainer 20 is attached to the upper surface 14 of the anchor pad 12. The base 22 desirably is secured to the upper surface 14 by a solvent bond adhesive, such as cyanoacrylate or other bonding material. One such adhesive is available commercially as Part No. 4693 from the Minnesota Mining and Manufacturing Company (3M).

As also seen in FIG. 4, the cover 24 has an elongate shape which desirably is coextensive with the planar size and shape of the base 22 (i.e., desirably has the same geometric shape and size as the base 22); however, the cover 24 need not be the same size or shape as the base 22. For instance, the cover 24 can be sized to extend beyond any of the lateral, traverse, or longitudinal edge of the base 22 or, alternatively, can be sized so as to not extend to the lateral, traverse, or longitudinal edge of the base 22. The cover can also include a skirt or flange that extends over and/or about the base 22 or any portion thereof.

The cover 24 though desirably has a sufficient size to cover the lower groove 30 in the base and to accommodate a portion of the latch mechanism 80 and the hinge 40 which operate between the base 22 and the cover 24, as described below. The cover 24 also desirably is of a dimension which provides for easy manipulation. For example, the cover's size easily accommodates the grasp of a medical attendant.

The cover 24 includes a first side 32 which lies generally at one lateral end of the cover 24. The first side 32 of the cover therefore generally corresponds to the first side 26 of the base 22. The cover 24 also has a second side 34. The second side 34 lies generally toward a lateral end of the cover 24, opposite of the first end, and corresponds generally to the second side 28 of the base 22.

An upper groove 36 is formed on an inner side of the cover 24 between the first and second sides 32, 34 of the cover 24 and corresponds generally to the lower groove 30 formed in the base 22. The width of the upper groove 36 is also varied in the lateral direction along its longitudinal length. That is, in the illustrated embodiment, the side walls of the upper groove 36 diverge from each other in a generally linear manner from one longitudinal end of the cover 24 to the other longitudinal end.

The cover 24 is flexibly coupled to the base 22 by way of a flexible coupling or hinge 40. The coupling 40 desirably comprises a flexible band 42 that can take any number of forms to mechanically connect the cover 24 to the base 22 while permitting pivotal movement of the cover 24 relative to the base 22 so as to enable engagement or disengagement of these parts, as described below. In the illustrated embodiment, the band 42 is formed of flexible material, desirably of the same material from which the base 22 and cover 24 are comprised. Advantageously, the hinge 40 is integrally molded with the base 22 and the cover 24 to form a unitary member, as noted above. The hinge 40 is located at an outer edge of the base 22 and the cover 24; however, the hinge 40 need not be laterally located at an extreme end of the base 22 or cover 24.

As best understood from FIG. 6, the width of the hinge 40, as measured in the longitudinal direction, is desirably less than that of either the base 22 or the cover 24 to allow some leeway or play when engaging or disengaging the cover 24 to the base 22. That is, this shape allows the hinge 40 to twist to some degree to compensate for some manufacturing tolerances; however, the hinge 40 can have at least as large of a longitudinal dimension as the base 22 and the cover 24.

The hinge 40 is desirably integrally formed along a common corresponding exterior surface of the cover 24 and base 22. In the illustrated embodiment, as best understood from FIG. 5b, the hinge 40 has generally a U-shape when the cover 24 is closed, and extends from both the base 22 and the cover 24 in the lateral direction to the side of the retainer 20. A gap 44, corresponding to a transverse height of the hinge 40, exists between the base 22 and cover 24. This gap 44, however, can be reduced or eliminated from the retainer for some applications by using a different hinge design.

Figure 5A:
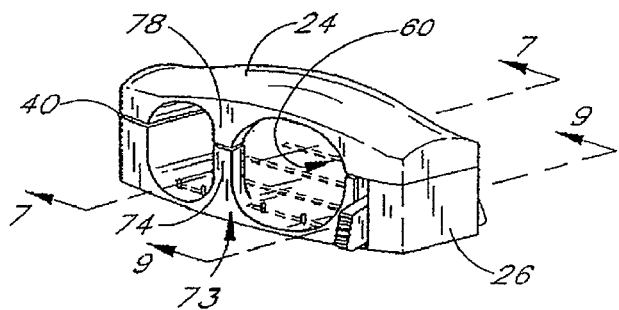
FIG. 5*a* is a perspective view of the retainer illustrated in FIG. 2 with the cover in a closed position.

The hinge 40 enables the cover 24 to move between the open position and the closed positions. The open position, as illustrated in FIG. 4, is characterized by exposing the grooves 30, 36 in the base 22 and the cover 24 in the transverse direction and thereby spacing apart the base 22 and the cover 24. When in the open position, the retainer 20 is capable of receiving a portion (e.g., the Y-site 112) of the Foley catheter 8. The closed position, as illustrated in FIG. 5a, is characterized by the cover 24 lying in contact or near contact with the base 22 so as to position the upper groove 36 above the lower groove 30. When in the closed position, the retainer 20 surrounds the received portion of the catheter.

Figure 5B:
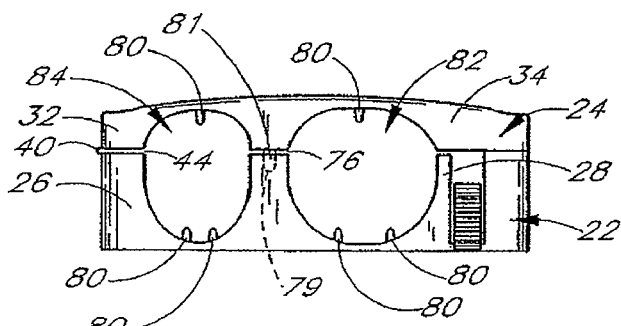
FIG. 5*b* is an elevational view of a distal end of the retainer of FIG. 5*a*.

The hinge 40 need not provide 180° of movement of the cover 24 relative to the base 22 to establish the closed position and a fully open position, as illustrated by FIGS. 5b and 6. For instance, the hinge 40 can permit a smaller degree of movement (e.g., 90°) between the base 22 and the cover 24 while still providing enough space to transversely insert the catheter into the retainer 20.

The grooves 30, 36 formed in the base 22 and the cover 24 define a channel 60 when the retainer 20 is closed. The channel 60 is capable of receiving a portion or length of the catheter 8 and is generally configured to house, grip and secure the affected catheter portion. The channel 60 can have a variety of configurations, as discussed above in connection with the grooves 30, 36, in order to accommodate a particular medical article. In the illustrated embodiment, the channel 60 generally has circular cross-sectional shape at its proximal end 62 and a generally oblong cross-sectional shape at its distal end 64 (although, in the illustrated embodiment, the distal end 64 is divided by a pair of cooperating post, which will be described below). The channel smoothly tapers in cross-sectional size from its smaller proximal end 62 to its larger distal end 64. The channel 60 consequently generally has a truncated V-shape, as best understood by inspecting the shapes of the grooves 30, 36 in FIG. 6.

Figure 6A:
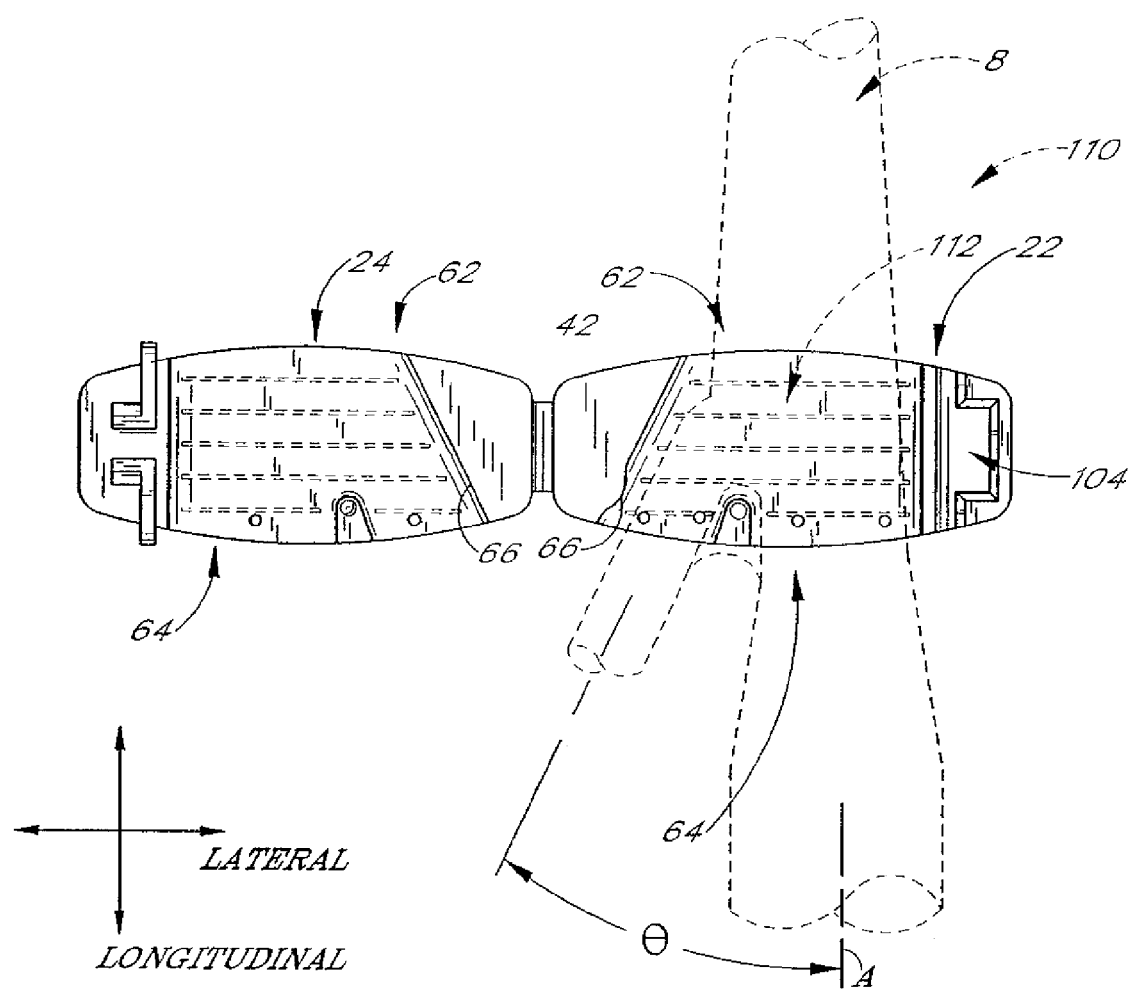
FIG. 6*a* is a top plan view of a retainer configured in accordance with a variation of the retainer shown in FIG. 6 and illustrates a channel groove on the base that includes a convex wall section.

In the embodiment illustrated in FIGS. 1-6, the sides of the channel 60 are generally straight and diverge from each other. The walls of the channel 60 (and, thus, the grooves of the cover and base), however, need not be straight. For example, as seen in FIG. 6a, the wall of the base groove 30 can have a convex section that narrows the portion of the channel that receives the inflation branch 114 of the catheter. This channel shape furthers retention of the catheter within the channel 60 to inhibit catheter movement through the channel, as discussed below.

Although the channel 60 can take the form of various shapes depending upon its application (i.e., depending upon a shape of the retained portion of the medical article for which the retainer is designed to be used), the channel 60 does have a sufficient length in the longitudinal direction to stabilize the catheter, rather than act as a fulcrum for the catheter, as mentioned above. That is, the retainer receives a sufficient length of the catheter to inhibit movement of the catheter in the lateral, longitudinal and transverse direction (i.e., to inhibit yaw, pitch and axial movement of the catheter), without kinking the catheter. Also, the wide-mouth shape (i.e., the large oval-shape) of the channel proximal opening eliminates an edge or surface over which the catheter could kink.

When the cover 24 is closed, a section of the catheter 8 is captured within the retainer 20. Thus, the retainer 20 at least restricts, if not prevents, lateral and transverse movement of the retained section of the catheter 8.

Inhibiting movement of the catheter 8 in the longitudinal direction when the catheter 8 is secured within the channel 60 is desirably accomplished by one or more retention mechanisms that associate with the channel 60. With reference to FIGS. 4, 5 and 6, one such retention mechanism involves the shape of the channel 60 itself. The interaction between the truncated V-shape of the channel 60 and a corresponding shape of the catheter Y-site 112 inhibits proximal longitudinal movement.

As best understood from FIG. 6, the proximal end 62 of the channel 60 is sized to receive only the main body 118 of the catheter 8. The distal end 64 of the channel 60 is sized to receive both branches 114, 116 (i.e., the inflation lumen section and the drainage lumen section) at the distal side of the Y-site 112. And between its distal and proximal ends 64, 62, the channel 60 is configured to receive the catheter Y-site 112. In the illustrated embodiment, a second side 68 of the channel 60 (formed by the second sides 28, 34 of the base 22 and the cover 24) lies generally parallel to a longitudinal axis of the portions of the catheter drainage lumen received by the channel 60; however, a first side 66 of the channel 60 (formed by the first sides 26, 32 of the base 22 and cover 24) is angled relative to the second side 68. The first side 66 of the channel 60 desirably varies in a tapering or linear manner (although it can include a convex section as noted above). An angle of divergence between the first and second sides 66, 68 of the channel 60 desirably is between about 10° and about 70°, and more preferably is between about 30° and about 45°, and generally matches an angle of intersect θ between the two branches 114, 116 of the catheter 8, as seen in FIG. 6.

Because the catheter Y-site 112 is large in cross-section than its main body 118 and because of the presence of a large valve which is attached to the catheter inflation branch (see FIG. 13), the Y-site 112 usually cannot be pulled proximally through the smaller proximal end 62 of the retainer channel

60. The shape of the channel 60 thus inhibits longitudinal movement of the catheter in the proximal direction.

Variations on the channel's shape of course are also possible, as noted above. For instance, the second side 68 of the channel 60 can vary from the first side 66 in a curvilinear manner and/or can include a gouge, protrusion (FIG. 6a) or similar geometric abnormality so as to cooperate with or impinge upon a corresponding portion of the received catheter length. Also, there is no requirement that only the first side 66 vary relative to an axis A of the received catheter length. Either the first 66 or second 68 side, or both sides, can vary in distance relative to the axis A of the received catheter length so as to inhibit longitudinal movement of the retained section of the catheter 8. The channel, however, can have a straight or uniform cross-sectional shape where the retainer includes at least another mode of the retention mechanism.

The interaction between the surface 69 of the retainer channel 60 and the catheter Y-site 112 also creates friction to inhibit longitudinal movement through the channel 60. The degree of interference between the catheter 8 and the retainer 20, however, cannot be so great as to significantly occlude the catheter 8.

Another retention mechanism to inhibit axial movement of the catheter 8 involves one or more friction ridges 70 located on the channel surface 69. In the illustrated embodiment, depicted by FIGS. 4 and 9, the ridges 70 are integrally formed with the base 22 and the cover 24 and project into the channel 60. Because the illustrated embodiment also includes securement barbs, which will be described below, the friction ridges 70 are illustrated in phantom to convey that the ridges 70 can be used together with or in the alternative to the securement barbs.

The ridges 70 are desirably of smooth solid construction; however, they can be of hollow construction. The ridges in the illustrated embodiment have generally triangular cross-sectional shapes and angle toward one end of the channel 60 (e.g., the distal end). The ridges 70, however, can have other cross-sectional shapes which would interfere with axial movement of the catheter 8 through the channel 60.

In the illustrated embodiment, as best seen in FIG. 6, each of the ridges 70 desirably has a front wall or leading edge 72 that forms an angle of less than 90 degrees as measured between the front wall 72 and the channel surface 69. The ridges 70 slightly protrude into the channel 60, desirably at a transverse distance of between 0.1 to 10 mm for the given application. As best seen in FIG. 6, the ridges 70 also lie generally normal to a longitudinal axis through the channel 60.

When so arranged, the friction ridges 70 gently, but securely bite or press into an outer surface of the catheter Y-site 112. Such contact does not occlude or otherwise meaningfully impair fluid flow in the catheter lumens because of the compliant nature of the catheter body material and because of the degree to which the ridges bite into the catheter body. This degree of contact, however, coupled with the angular orientation of the ridges inhibits movement of the catheter 8, especially in a direction opposite of that in which the ridges are angled.

A retaining structure 73, which protrudes into the channel 60, can also be used to inhibit axial movement of the catheter. The retaining structure 73 forms an upstanding member transversely positioned relative to the anchor pad 12. The retaining structure 73 is arranged to lie between the branches at the catheter Y-site 112 retained by the retainer 20 so as to inhibit axial movement of the catheter 60 in the distal direction. Thus, in the illustrated embodiment, the combination of the tapering channel shape and the retaining structure 73 inhibits axial movement of the retained section of the catheter 8 in both the proximal and distal directions.

The retaining structure 73 desirably has a sufficient height to inhibit axial movement of the catheter 8 in the distal direction. For this purpose, the retaining structure 73 has a height, in the transverse direction, of at least about 25% of the height of the channel 60 at the location at which the structure is positioned. In the present application, the retaining structure desirably extends across channel 60.

In the illustrated embodiment, the retaining structure 73 is formed by a base post 74 and a cover post 78. The base post 74 desirably is integrally formed with the base 22, and is located in the channel 60 toward the distal end 64 of the channel 60. The cover post 78 is integrally formed with the cover 24 also at the distal end 64 of the channel 60. Although in the illustrated embodiment, the base post 74 and cover post 78 lie within the channel 60, the posts 74, 78 can be located outside the distal end 64 of the channel 60.

In one mode, the base post 74 is sized to extend to a position where its upper end lies near or contacts the webbing 120 of the catheter 8 that extends between the Y-site branches 114, 116. In the illustrated embodiment, the upper end of the post 74 lies generally even with the upper surface of the first and second sides 26, 28 of the base 20, as best seen in FIG. 4. The cover post 78 similarly extends to a point which is generally flush with a plane defined by the inner surfaces of the cover first and second sides 32, 34 that lie adjacent to the base 22.

As best seen in FIG. 6, the lateral position of the post 74 within the channel 60 corresponds with the merge point between the inflation lumen branch 114 and the discharge lumen branch 116 of the Foley catheter 8. The post 74 divides the channel 60 at the channel's distal end 64.

The cover post 78 is configured and arranged on the cover 24 in a manner similar to that described above in connection with the post 74 on the base 22. In the illustrated embodiment, the post 78 thus generally opposes the base post 74. By this particular design, as understood from FIG. 6, the combination of the posts 74, 78 and the channel 60 define a generally Y-shaped recess between the channel's proximal and distal ends 62, 64.

In the illustrated embodiment, the transverse height of the cover post 78 is less than that of the base post 74. The posts 74, 78, however, can have equal heights or the cover post 78 can be longer than the base post 74. Together though, as best seen in FIG. 5b, the posts 74, 78 desirably span the channel 60 in the transverse direction, except for a small gap 76 formed at their interface. This gap 76 can be slightly less than a thickness of the catheter webbing 120 between the Y-site branches 114, 116, for the reasons described below, and corresponds to the gap 44 provided by the hinge 40 when the cover 24 is closed.

The posts 74, 78 thus extend between these two branches 114, 116 of the catheter 8 when the catheter Y-site 112 is positioned within the channel 60. Together the posts 74, 78 can act as a stop against longitudinal movement of the catheter 8 in the distal direction. That is, longitudinal movement in the distal direction causes the catheter Y-site 112 to contact the posts 74, 78. The posts 74, 78, being of rigid construction, prevent further longitudinal movement.

Although the posts 74, 78 can have a variety of cross-sectional shapes, the posts 74, 78 desirably have a generally triangular cross-sectional shape in the present application so as to correspond to the space between the two catheter branches 114, 116 at the Y-site 112. The proximal edge of the posts, however, advantageously is rounded to eliminate sharp contact between the catheter 8 and the retainer 20 at this location.

The posts 74, 78 can also include interengaging elements to interlock the posts 74, 78 in the transverse direction and prevent the catheter 8 from being pulled through the gap 76 between their ends. In the illustrated embodiment, a pin or projection 81 and a corresponding receptacle 79 are arranged between the interfacing ends of the posts 74, 78. As best seen in FIGS. 4, 5b and 6, the receptacle 79 is formed at the transverse end of the base post 74, extending into the post 74 in a transverse direction from an interface surface of the post 74. The projection 81 extends from an end of the cover post 78 in a direction parallel to a transverse axis of the post 78. The projection 81 is configured to fit within the receptacle 79. When the cover 24 is closed, the pin 81 extends into the receptacle 79 to interlock together the posts 74, 78.

Another possible retention mechanism to inhibit axial movement of the catheter 8 relative to the retainer 20 involves protuberances that are arranged to cooperate with one another when the cover 24 is closed. For instance, in one mode, the cooperating posts 74, 78 can be arranged to capture a structural portion of the catheter (e.g., the catheter webbing 120) between them without substantially occluding an inner lumen of the catheter 8, as schematically represented in FIG. 6. In another mode, the projection 81 can be employed without the receptacle 79 to simply pin a portion of the catheter (e.g., its webbing) against a surface of the retainer 20. For instance, the projection 81 can extend from a portion of either the base 22 or the cover 24 and cooperate with a corresponding surface (be it a post, platform or channel surface) that opposes the projection 81 when the cover is closed. The projection 81 would protrude into the portion of the catheter and pin it against the corresponding surface.

Alternatively, the projection 81 can be used with the receptacle 79 to capture a section of the catheter. When the cover 24 is closed, the projection 81 could force a portion of the catheter body 8 into the receptacle 79 to capture a structural portion of the catheter 8 between these components without occluding an inner lumen of the catheter. This engagement of the retainer 20 with the catheter body 8 would inhibit axial catheter movement relative to the retainer 20.

One or more securement barbs 80 can also be used to retain the catheter in the longitudinal direction. In the illustrated embodiment, each barb 80 has a generally conical shape with a blunt tip. The barb 80, in the present application, desirably extends into the channel 60 by an amount ranging between about 0.1 mm and about 3 mm.

The retainer desirably includes at least one set of securement barbs 80, indicated collectively by reference numeral 82, which are arranged within the channel 60 to cooperate with one another. The barbs 80 advantageously are arranged within the same general lateral plane (i.e., a plane defined by the lateral and transverse axes), and are spaced apart from one another. In addition, the barbs 80 desirably are spaced on generally opposite surfaces 69 of the channel 60 in a staggered arrangement. That is, the position of the barbs 80 alternate between the cover surface and the base surface in the lateral direction. The resulting overlapping pattern of the barbs 80 securely holds the catheter 8 without imparting torque to the catheter 8 if pulled in a longitudinal direction. In the illustrated embodiment, one barb 80 is positioned on the cover surface and is generally equally distanced in the lateral direction from the adjacent side of the channel 60 and the adjacent side of the post 78. A pair of barbs 80 is positioned on the base surface. These barbs 80 are spaced apart from one another and the pair is symmetrically positioned relative to a transverse axis that extends through the barb 80 on the cover surface.

Figure 7:
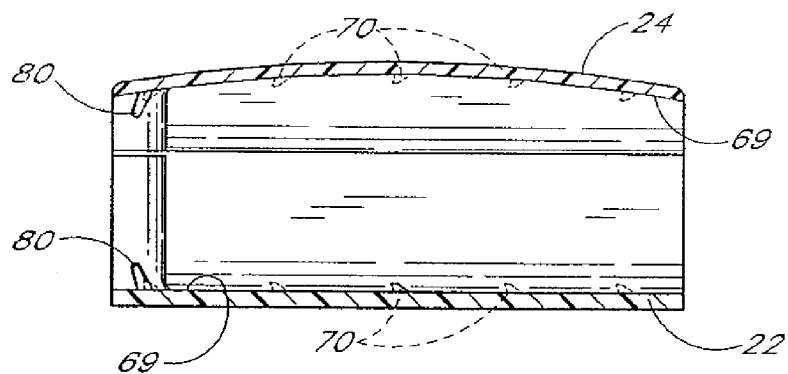
FIG. 7 is a cross-sectional view of the retainer of FIG. 5*a*, taken along the line 7-7.

The present retainer 20 also includes a second set of securement barbs, indicated collectively by reference numeral 84 (see FIG. 5), which are arranged generally in accordance with the above description; however, fewer number of barbs, as well as fewer sets, can also be used. In the illustrated embodiment, one set of barbs 84 is placed between the posts 74, 78 and the first sides 26, 32 of the cover 24 and the base 22, and the other set of barbs 82 is placed between the posts 74, 78 and the second sides 28, 34 of the cover 24 and the base 22. As best seen in FIG. 7, the barbs of the first set 84 are desirably angled toward the distal end 64 of the channel 60 to inhibit movement of the catheter's inflation lumen branch 114 in the proximal direction when the catheter 8 is pulled proximally, as well as when the catheter 8 discharge branch 116 is pulled distally. The barbs of the second set 82, however, are desirably angled toward the proximal end 62 of the channel 60 to inhibit movement of the catheter 8 when the catheter's discharge branch 116 is pulled distally.

Figure 9:
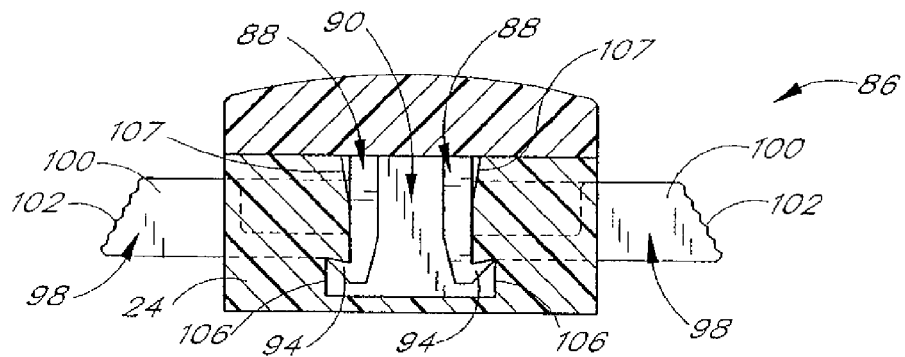
FIG. 9 is a cross-sectional view of the retainer of FIG. 5*a*, taken along the line 9-9.
Figure 8:
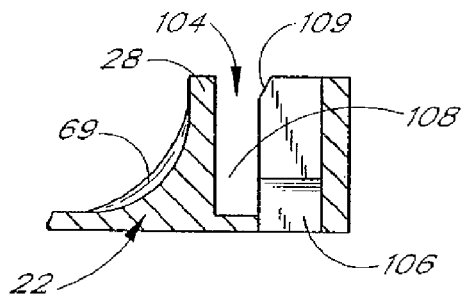
FIG. 8 is a cross-sectional view of a latch receptacle of the retainer illustrated in FIG. 6, taken along the line 8-8.
Figure 10:
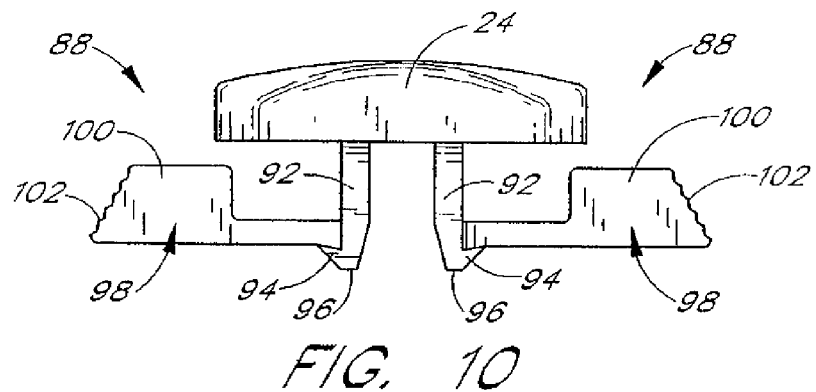
FIG. 10 is a partial side elevational view of the retainer of FIG. 6 as viewed in the direction of line 10-10, and illustrates the cover and an associated latch mechanism of the retainer.

To firmly hold the affected catheter portion within the channel, the base 22 and the cover 24 include interengaging structure to couple them together in the closed position. In the illustrated embodiment, as best seen in FIGS. 8-10, a latch mechanism 86 is used to secure the cover 22 to the base 24. The latch mechanism 86 comprises at least one moveable keeper 88 and at least one latch 90. The keeper 88 is arranged on the cover 24 while the latch 90 is arranged on the base 22; however, these components can be flip-flopped on the base and the cover.

As best seen in FIG. 10, each keeper 88 includes a bar 92 extending toward the base 22 from the second side 39 of the cover 24. A tang 94 is formed at a lower end 96 of the bar 92. Desirably, the lower end 96 of the bar 92 is relatively blunt and smooth to prevent it from puncturing the gloves or skin of a healthcare provider or catching on other materials. An operator lever 98 extends to the side of the bar 92 and includes an enlarged platform or ear 100 at its outer end. The platform 100 desirably include ridges or knurls, as seen in FIG. 10, on an inclined surface 102. The inclined surface 102 slopes outward in a direction toward the base 22 such that a component of a transverse force applied to the surface 102 will cause the bar 92 to deflect inward. The entire keeper 88 desirably is formed with the cover 24 to form a unitary piece.

The latch mechanism 86 includes a receptacle 104 that receives the bar 92 and the tang 94. The latch receptacle 104 includes an inner notch 106 into which the tang 94 snaps when the cover 24 is in the closed position; however, the tang can be arranged in the receptacle and the notch be positioned on the bar to accomplish the same effect. The latch 90 desirably is formed with the base 22 as a unitary piece.

In the illustrated embodiment, as best seen in FIG. 10, the cover includes two keepers 88 that are mirror-images of each other. And, as best seen in FIG. 7, the latch 90 includes two notches 106, each of which is arranged to receive one of the keeper tangs 94 when the cover 24 is closed.

An entrance of the receptacle 104 includes chamber edges 107. The chamfer edges 107 slope inward toward the center of the receptacle 104 to cause the keeper bars 92 to bend inward when inserting the keepers 88 into the latch receptacle 104.

As best understood from FIGS. 6, 8 and 9, the second side 28 of the base 22 also includes a slot 108 to receive a portion of the operator levers 98 and the bars 92 of the keepers 88 when the associated tangs 94 are inserted into the receptacle 104. The entrance to the slot 108 also includes a chamfer 109 on its outer edge to facilitate insertion of the keeper levers 98 into the slot 108.

In operation, the cover 24 can swing toward the closed position. The relatively thin strip of material forming the coupling allows the hinge 40 to bend when finger pressure is exerted on the cover 24 to close it. The lower ends 90 of the keeper bars 92 contact the chamfered edges 107 of the latch receptacle 104 when the cover 24 nears its closed position. Continued pressure forces the bars 92 inward (toward each other) to permit the tangs 94 to pass through a narrow section of the receptacle. The slot 108 of the receptacle 104 receives the operator levers 98 as the tangs 94 are pushed further into the receptacle 104. The tangs 94 snap into the notches 106, under the spring force provided by the deflected bars 92, when the cover 22 sits atop the base 24. The interaction between the tangs 94 and the corresponding surfaces of the notches 106 hold the cover 24 in this position.

As best seen in FIG. 9, the operator levers 98 extend to the longitudinal sides of the base 24 when the cover 24 is latched. The platforms 100 thus remain exposed.

A medical attendant presses downward on the platforms 100 to open the latch mechanism 80. A downwardly force applied to the angled outer surface 102 exerts an inward force component which deflect the corresponding bar 92 inward and release the tangs 94 from the notches 106. The inherent spring force stored in the bent hinge band 42 assists with providing a transverse force that moves keepers 88 out of the receptacle 104. The medical attendant can then open the cover 24 and expose the inner grooves 30, 36 of the base 22 and the cover 24.

The releasable engagement between the cover 24 and the base 22 allows the same retainer 20 to be used for an extended period of time, while permitting repeated attachment and reattachment of the catheter to the anchoring system 10. In addition, the hinged connection connecting the cover 24 to the base 22 ensures that the cover 24 will not be lost or misplaced when the catheter is detached from the anchoring system 10. The medical attendant wastes no time in searching for a cover, nor in orienting the cover prior to latching.

Figure 11:
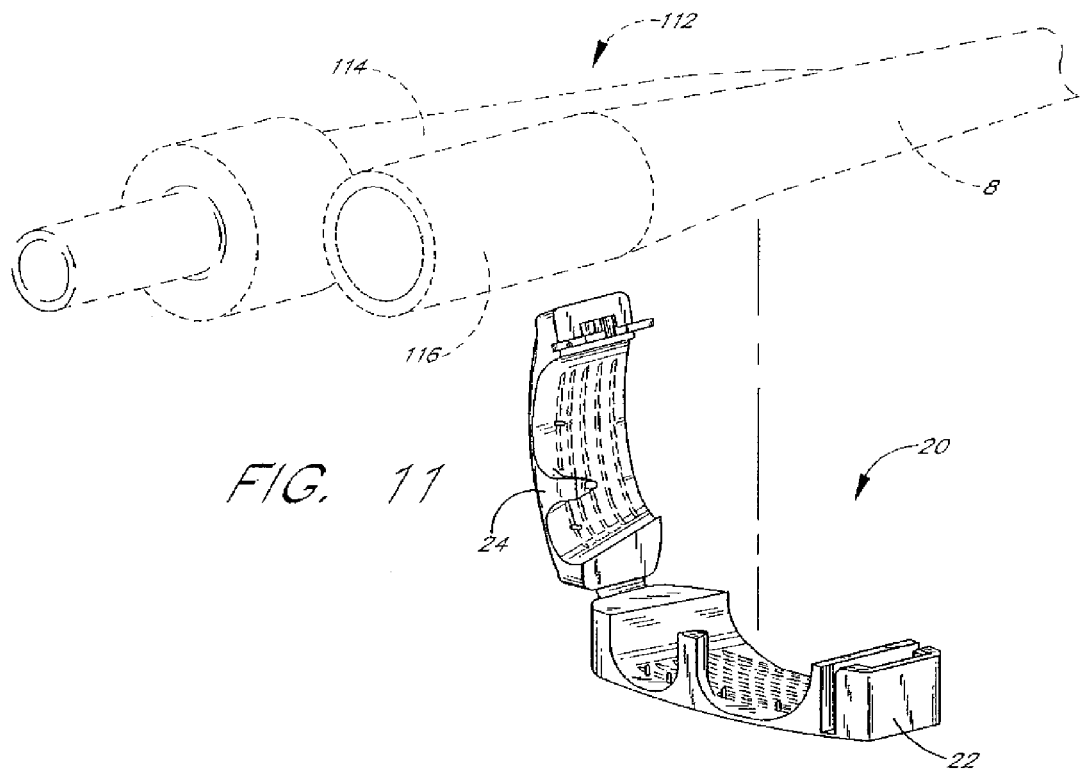
FIG. 11 is a perspective view of the anchoring system of FIG. 1, and illustrates the cover in an open position and a catheter aligned above the anchoring system for insertion therein.
Figure 12:
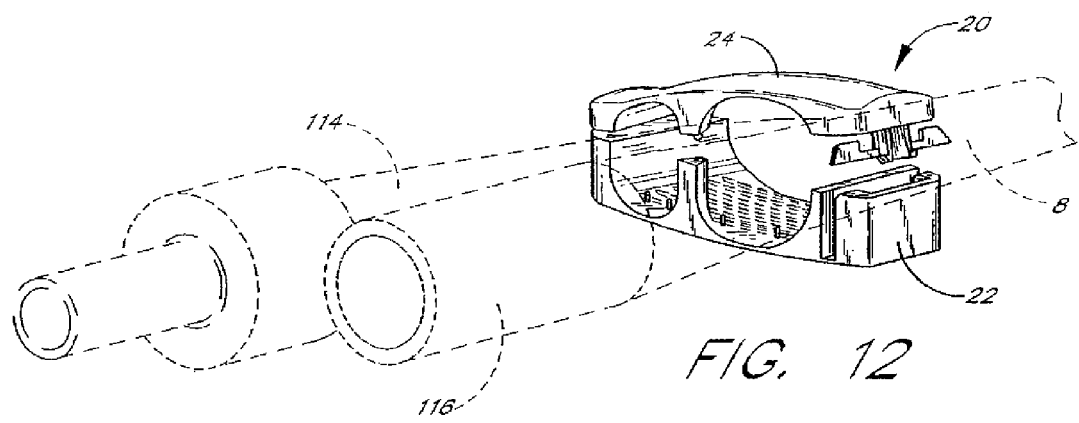
FIG. 12 is a perspective view of the anchoring system of FIG. 1, and illustrates the cover in a partially closed position with a channel formed by the cover and base of the anchoring system receiving the catheter.
Figure 13:
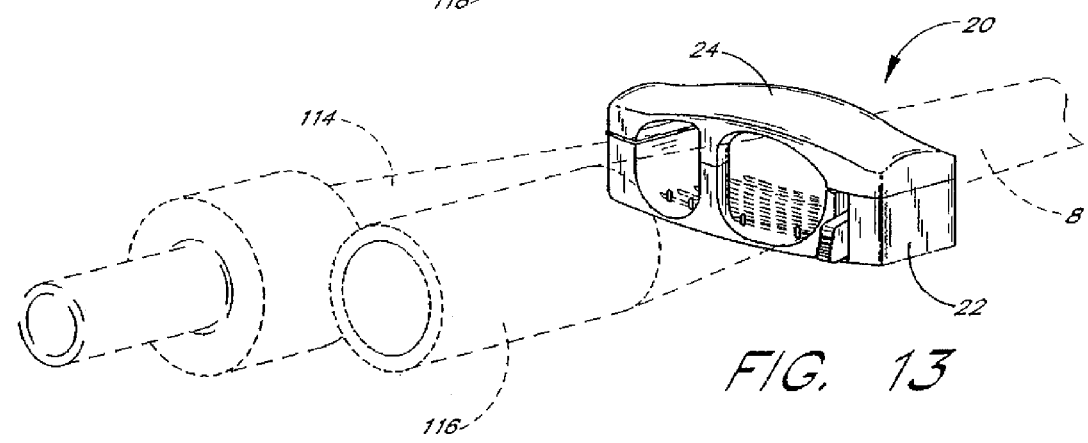
FIG. 13 is a perspective view of the anchoring system of FIG. 1, and illustrates the cover in a closed position with the catheter secured within the channel of the anchoring system.

As illustrated in FIGS. 11-13, a medical attendant can secure a Foley catheter (or other medical article) to a patient using the above-described anchoring system (or a readily apparent modification thereof). The medical attendant first opens the retainer 20 to expose the groove 30 on the base 22. Once opened, a catheter 8 can be transversely aligned over the groove 30. The catheter 8 can then be placed into the channel 60. If the channel 60 is formed with a post 74 (or another protuberance) for use with a Y-site, the first and second branches 114, 116 are aligned around the post 74 and the catheter Y-site 112 is aligned to securely fit within the remaining groove confines. Once the catheter 8 is so aligned and placed into the groove 30, the cover 24 is closed and latched, in the manner described above. The shapes of the grooves 30, 36 ensure that the channel supports the catheter Y-site 112 on at least diametrically opposed sides thereof along the entire retained length of the catheter Y-site. This not only enhances frictional contact between the retainer 20 and the catheter 8, but it also prevents the catheter 8 from kinking or crimping with the retainer 20 and thereby occluding one or more of the catheter lumens.

In the illustrated embodiment, the posts 74, 78 come together with the projection 81 inserting into the receptacle 79 when the cover is closed. The posts 74, 78 therefore are interlocked in this position to form a stop on the distal side of the Y-site 112 that spans entirely across the channel's transverse length. The securement barbs 80 also bite into the body of the catheter Y-site 112 to resist movement of the catheter branches 114, 116 in a direction opposite of the direction in which they are angled.

If the catheter 8 is pulled in the proximal direction, the tapered shape of the channel 60 prevents the larger distal end of the Y-site 112 and the valve on the inflation branch 114 from pulling through the retainer. The second set of securement barbs 84, which bite into the inflation lumen branch 114, also inhibit movement of the catheter in this direction. And if the retainer employs posts or projections that clamp onto or pin the catheter webbing within the channel, then this engagement between the retainer and the catheter would further secure the catheter in place.

If the catheter discharge branch 116 is pulled in the distal direction, the interlocked posts 74, 78 inhibit this movement. The first set of securement barbs 82 bite into the discharge branch 116 and also oppose movement of the catheter branch 116 in this direction. A distal pulling force on the discharge branch 116 also tends to pull the inflation lumen branch 114 around the posts 74, 78. The second set of securement barbs 84 also inhibits this reaction to further anchor the catheter Y-site 112 within the retainer 20.

The retainer 20 thus inhibits longitudinal movement of the catheter 8 relative to the retainer, even when used with a lubricated catheter. The holding effect provided by each of the retention mechanisms, however, does not substantially occlude the lumens of the catheter. The interaction of the protuberances (i.e., the posts and/or projection) only affects the catheter webbing 120 (or like structure) and does not bear against the catheter body. Likewise, the interaction between the shape of the channel and posts restricts movement of the catheter in both axial directions, but does not crimp or kink the catheter body when it is inserted within the channel and about the posts. And although the securement barbs bear against the catheter body, their limited bite does not significantly occlude or penetrate the corresponding catheter lumen.

The illustration of the retainer as including all of the above-described forms of the retention mechanisms is merely exemplary. The retainer can include only one retention member or possibly several; it need not include all. In addition, any combination of the retention members in the retainer is also possible.

The present anchoring system thus provides a sterile, tight-gripping, needle- and tape-free way to anchor a medical article to a patient. The retainer thus eliminates use of tape, and if prior protocol required suturing, it also eliminates accidental needle sticks, suture-wound-site infections and scarring. In addition, the retainer can be configured to be used with any of a wide variety of catheters, tubes, wires, and other medical articles. Patient comfort is also enhanced and application time is decreased with the use of the present anchoring system.

A retainer in accordance with another embodiment of the invention is illustrated in FIGS. 14-20. Though not illustrated, this retainer also desirably used with a flexible anchor pad, as shown in FIGS. 1 and 3, to form the present anchoring system. The principal difference between this embodiment and the previous embodiment of the retainer lies in the interengaging structure between the retainer's base and cover. Accordingly, the above description applies equally to the embodiment of FIGS. 14-20, unless otherwise indicated. In addition, like reference numerals are used to indicate like features to the two embodiments, with the letter designation "a" added as a suffix to refer to particular features of the present embodiment.

The principles of the interengaging structure of the present embodiment to provide for releasable engagement between the base 22a and cover 24a of the retainer 20a are similar to the principles of the previous embodiment. However, the particular structure and arrangement of the interengaging structure used to accomplish these principles differs, as described below. Like the previous embodiment, the interengaging structure of this retainer 20a uses a latch mechanism 86a (FIG. 14) comprising a keeper 88a (FIG. 15) and a moveable latch 90a (FIG. 15). The keeper 88a is arranged on the cover 24a while the latch 90a is arranged on the base 22a; however, these components can be alternatively disposed (i.e., flip-flopped) on the base 22a and the cover 24a. The latch mechanism 86a desirably is formed with the base 22a as a unitary piece.

Figure 15:
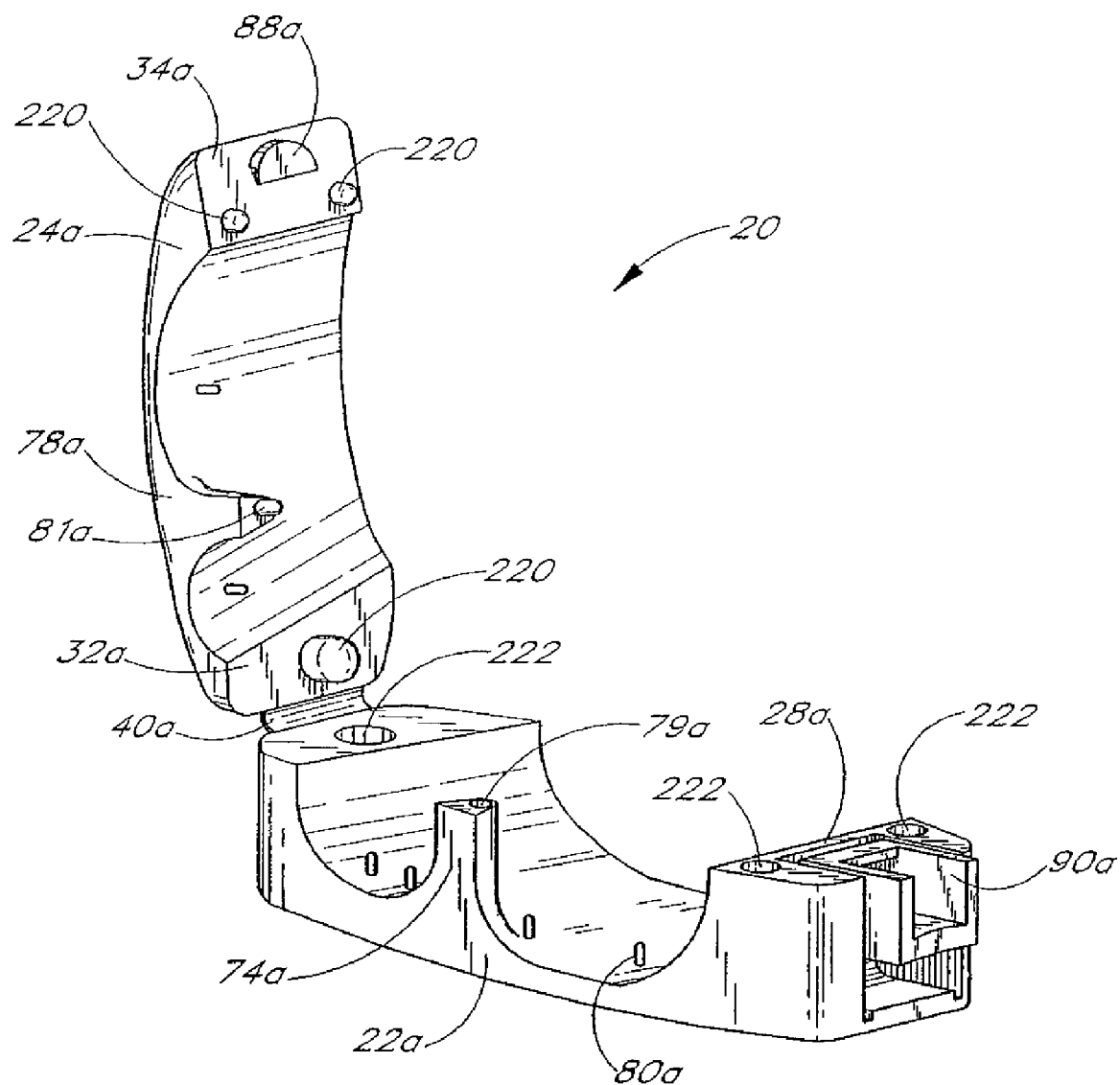
FIG. 15 is a perspective view of the retainer of FIG. 14, illustrating the retainer in the open position.
Figure 16:
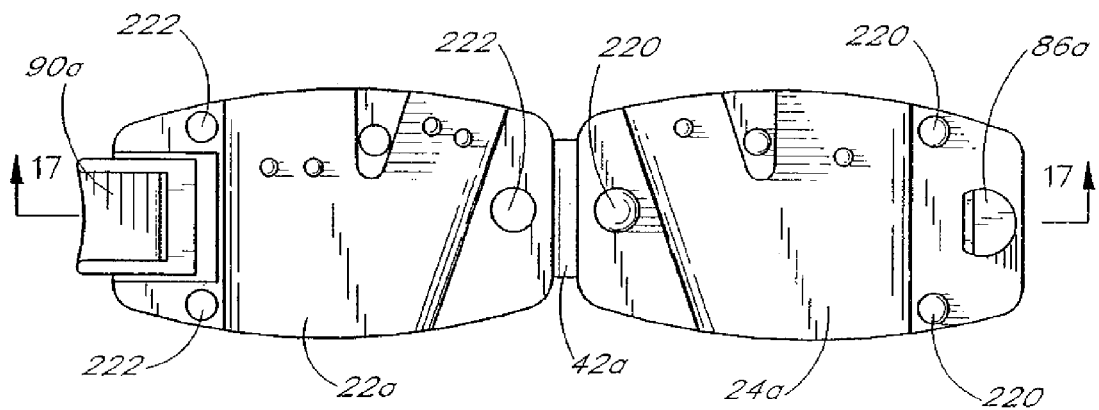
FIG. 16 is a top plan view of the retainer of FIG. 14, illustrating the retainer in the fully open position.
Figure 17:
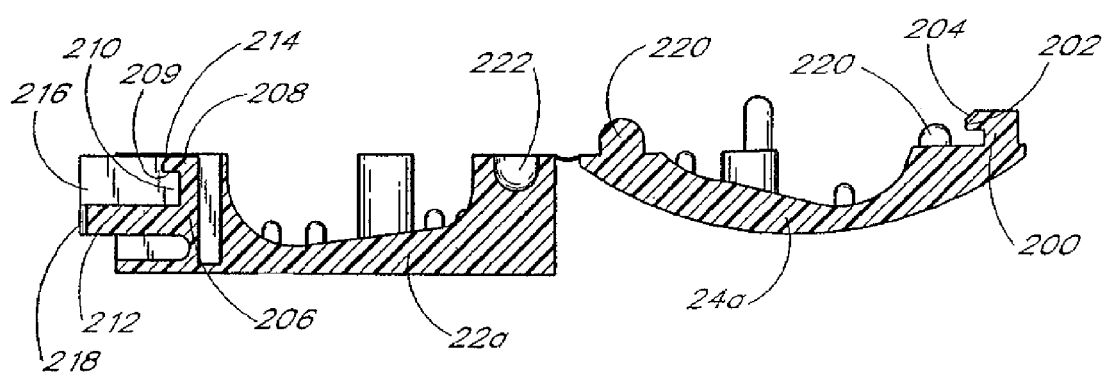
FIG. 17 is a cross-sectional view of the retainer of FIG. 14 taken along line 17-17, illustrating a latch mechanism.

As best seen in FIGS. 15-17, the keeper 88a depends from the cover 24a. The illustrated keeper 88a is generally L-shaped, having a first bar 200 extending toward the base 22a from the second side 34a of the cover 24a when the cover 24a is in the closed position. The keeper 88a also has a second bar 202 formed at a lower end of the first bar 200. Desirably, the lower end of the second bar 202 is relatively blunt and smooth to prevent it from puncturing the gloves or skin of a healthcare provider or catching on other materials. The keeper 88a, however, need not be generally L-shaped, but rather can be generally C-shaped, generally J-shaped, comprise a singular angled bar or the like.

The second bar 202 includes a chamfer along at least a portion of the inner edge 204. The chamfer edge 204 slopes away from the center of the channel 60a to assist in releasably engaging the base 22a and cover 24a, as explained below.

FIGS. 15-17 also show the interengaging structure further comprising a latch 90a extending from the second side 28a of the base 22a. The latch has an actuating bar 206, a tang 208, a recess 210, and an operator lever 212.

The actuating bar 206 extends from the base 22a and couples the base 22a to the other elements of the latch 90a. The actuating bar 206 is configured so that at least a portion of the bar 206, desirably the upper portion, can bend or give in the lateral direction when a suitable lateral force is applied. This configuration allows the tang 208 to bend inward when the keeper 88a contacts the tang 208 so that the keeper 88a can advance over the tang and into the recess 210, as detailed below.

The tang 208 extends from the actuating bar 206 in the lateral direction. The tang 208 defines a ridge having an underside 209 which is suitably sized to accept and retain the keeper 88a, as described below. The free lateral edge of the tang 208 includes a chamfer 214. The chamfered edge 214 slopes away from the center of the channel 60a to facilitate insertion of the keeper 88a into the latch 90a and thereby assist in releasably engaging the base 22a and the cover 24a.

The recess 210 is arranged to receive at least a portion of the second bar 202 of the keeper 88a when the cover 24a is moved to the closed position. The recess 210 provides an open area defined by the actuating bar 206, the tang 208 and the operator level 212. The recess 210, however, can be arranged on the keeper 88a and the second bar 202 arranged on the latch 90a to accomplish the same effect.

The operator lever 212 extends from the actuating bar 206 in the lateral direction and desirably protrudes beyond the second side 28a of the base 22a to allow a component of a suitable force to deflect the actuating bar 206 in the lateral direction toward the center of the channel 60a. The operator lever 212 desirably has a hollow region 216 adjacent the recess 210 to accept at least a portion of the keeper 88a when the retainer 20a is moved to the closed position. The illustrated operator lever 212 is generally U-shaped; however, a variety of other configurations can be used. The free lateral edge 218 of the operator lever 212 can include a curvature to generally match the curvature of a fingertip to assist the medical attendant in pushing on the operator lever 212 and for other ergonomic purposes. The free end 218 can also include ridges or knurls (not shown), to assist in maintaining secure contact between the medical attendant's finger tip and the operator lever 212.

Figure 18:
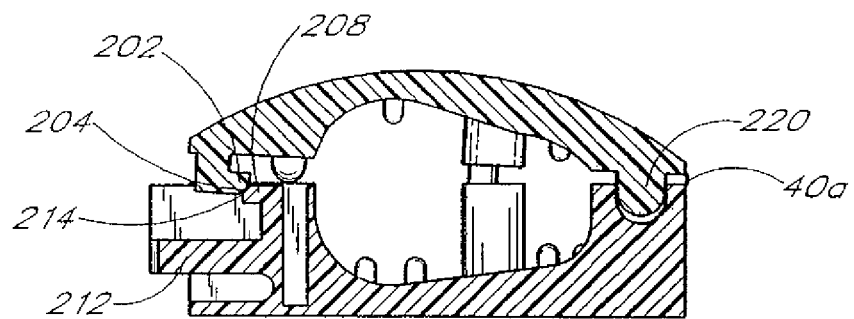
FIG. 18 is a cross-sectional view of the retainer of FIG. 17, with the cover moved towards a closed position.
Figure 19:
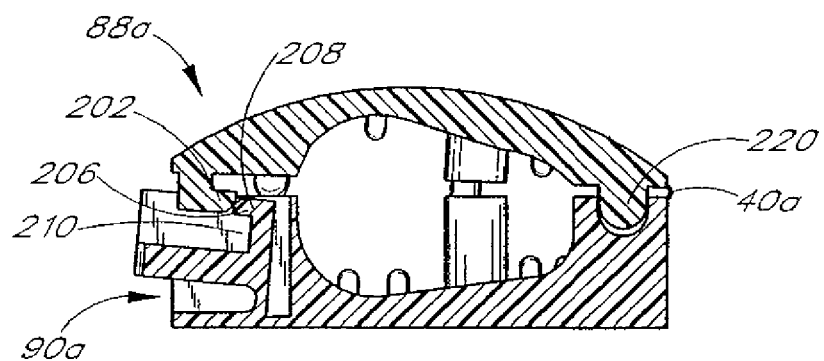
FIG. 19 is a cross-sectional view of the retainer of FIG. 17, with the cover in a partially closed position and the components of the latch mechanism beginning engagement.
Figure 20:
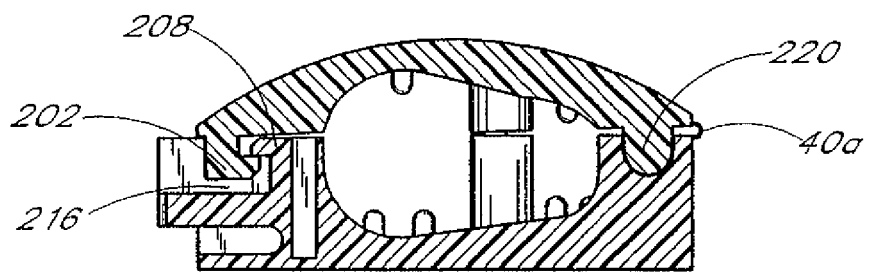
FIG. 20 is a cross-sectional view of the retainer of FIG. 17, illustrating the cover in a fully closed position and the components of the latching mechanism engaged.

As shown in FIGS. 17-19, in operation, the cover 24 can swing from the open position toward the closed position. The relatively thin strip of material forming the hinge 40a bends when finger pressure is exerted on the cover 24a to close it. As the cover 24a nears its closed position, at least a portion of 88a the keeper advances into the hollow 216 of the operator lever 212, and the chamfer edge 204 of the second bar 202 of the keeper 88a contacts the chamfer edge 214 of the tang 208 of the latch 90a. Continued pressure on the cover 24a is transferred through the chamfers 204, 214 to the actuating bar 206, and forces the tang 208 and the actuating bar 206 to deflect inward toward the channel 60a. These forces also cause the first bar 200 of the keeper 88a, and thus the second bar 202, to deflect outward, i.e., away from the channel 60a. The recess 210 then receives at least a portion of the second bar 202 of the keeper 88a as the keeper 88a is pushed further into the hollow 216. In this manner, at least portion of the latch 90a (e.g. tang 208) acts as a gatekeeper or moveable entranceway which selectively allows for passage of at least a portion of the keeper 88a (e.g. second bar 202) into the recess 210.

When the second bar 202 extends below the tang 208 and the cover 22a sits atop the base 24a, the actuating bar 206 and the first bar 200 snap back under the spring force provided by their deflection to position the second bar 202 beneath the tang 208. In this position, the keeper 88a and the latch 90a are interlocked together as the tang 208 obstructs passage of the second bar 202 through the entranceway. The interaction between the keeper 88a and the latch 90a, together with the obstructed passage, holds the base 22a and cover 24a in this closed position.

To open the latch mechanism 86a, the medical attendant presses on the operator lever 212 in the lateral direction so that the operator lever 212 exerts an inward force that deflects the actuating bar 206 in the lateral direction toward the channel 60a. Inward deflection of the actuating bar 206 inwardly deflects the tang 208, which, in turn, opens the entranceway so that the second bar 202 can be released from the recess 210. The medical attendant can then open the cover 24a and expose the inner grooves 30a, 36a of the base 22a and the cover 24a.

Referring back to FIGS. 14-16, a transverse force can be used to open the cover 24a and assist in moving the keeper 88a away from the latch 90a. The transverse force can be applied through a variety of mechanisms. One such mechanism involves the hinge 40a, where the inherent spring force stored in the bent hinge band 42a provides the suitable transverse force. Another such mechanism involves one or more interengaging elements arranged between interfacing portions of the base 22a and the cover 24a. The illustrated embodiment shows three sets of interengaging elements, one set arranged near the hinge 40a and two sets arranged near the latch mechanism 86a. Each set of interengaging elements include a pin 220 that depends from the cover 24a and a receiver 222 that recedes into the base 22a. The pin 220 is configured to fit within the recess 222 so that when the cover 24a is closed, the pin 220 extends into the recess 222 to interlock the base 22a and cover 24a together. The transverse length of the pin 220 is desirably sized slightly larger than the transverse depth of the receiver 222 (e.g. about 0.05-0.5 mm). By this arrangement, when the cover 24a is in the closed position, the first side 32a of the cover 24a is offset from (i.e., not in contact with) the first side 26a of the base 22a. Thus, the internal spring force stored in the interengaging elements can also provide the suitable transverse force to assist in opening the cover 24a. The interengaging elements also serve to interlock the base 22a and the cover 24a in the longitudinal and lateral directions, similar to that of the projection 81a and receptacle 79a of the previous embodiment.

The releasable engagement between the cover 24a and the base 22a allows the same retainer 20a to be used for an extended period of time, while permitting repeated attachment and reattachment of the catheter to the anchoring system 10a. In addition, the hinged connection connecting the cover 24a to the base 22a ensures that the cover 24a will not be lost or misplaced when the catheter is detached from the anchoring system. The medical attendant wastes no time in searching for a cover in orienting the cover prior to latching.

Figure 14:
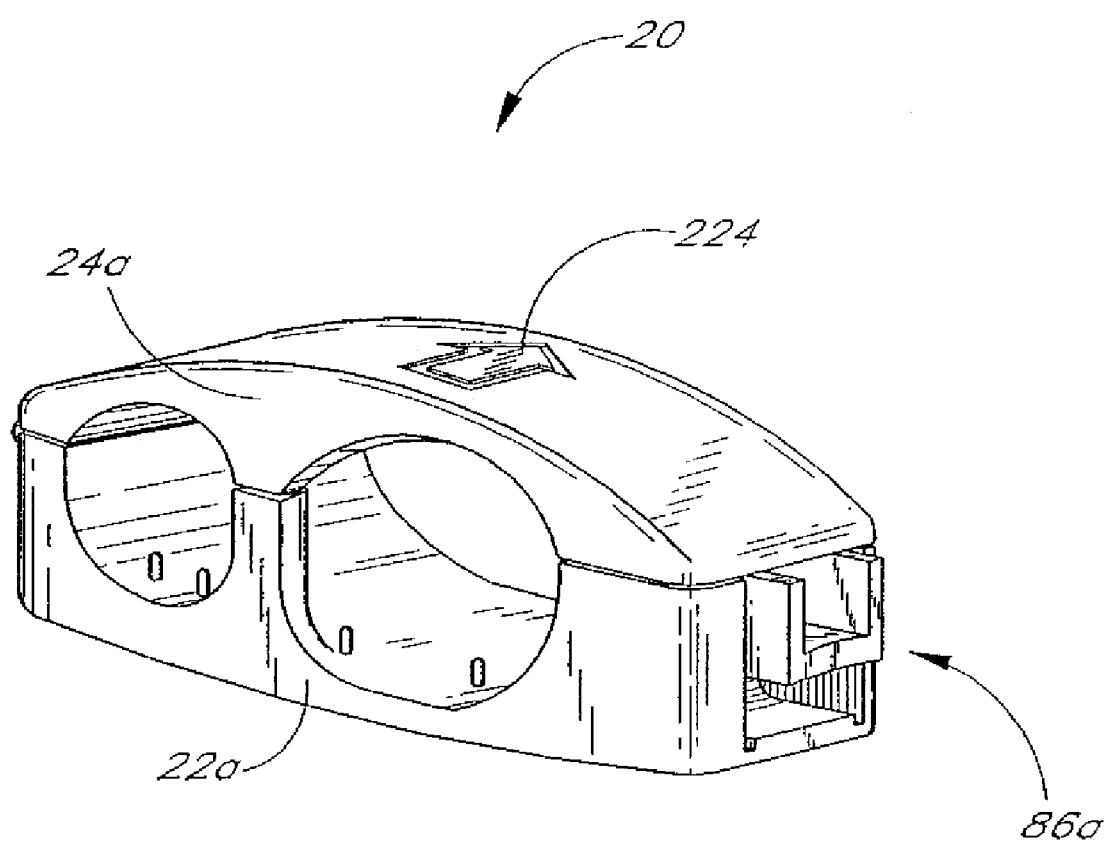
FIG. 14 is a perspective view of a retainer in accordance with another additional embodiment of the present invention.

FIG. 14 shows the top of the cover 24a having indicia 224 such as a directional arrow, to orient the medical attendant. The indicia 224 directs the positioning of the retainer 20a with respect to the catheter and the patient. The retainer 20a is desirably arranged so that the arrow points toward the catheter insertion point.

Figure 21:
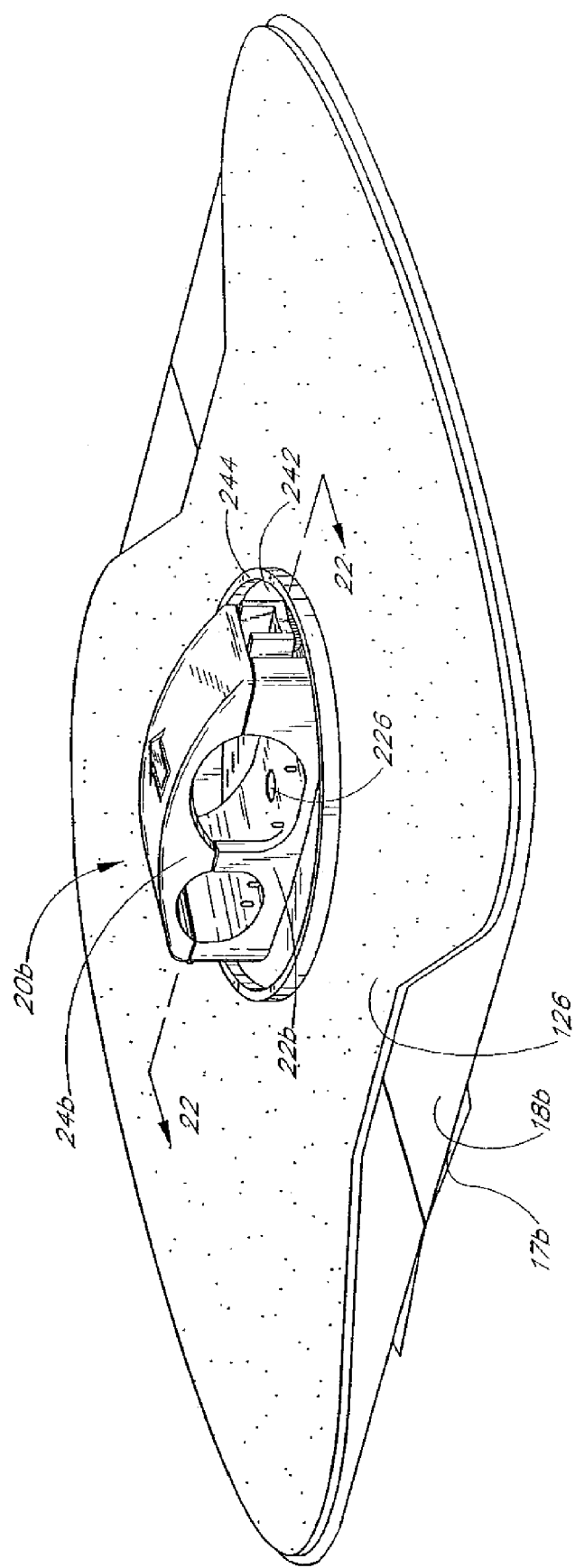
FIG. 21 is a is a perspective view of another preferred embodiment of the anchoring system of the present invention and illustrates the anchoring system from a distal end with a retainer rotatably mounted on a mount base.
Figure 22:
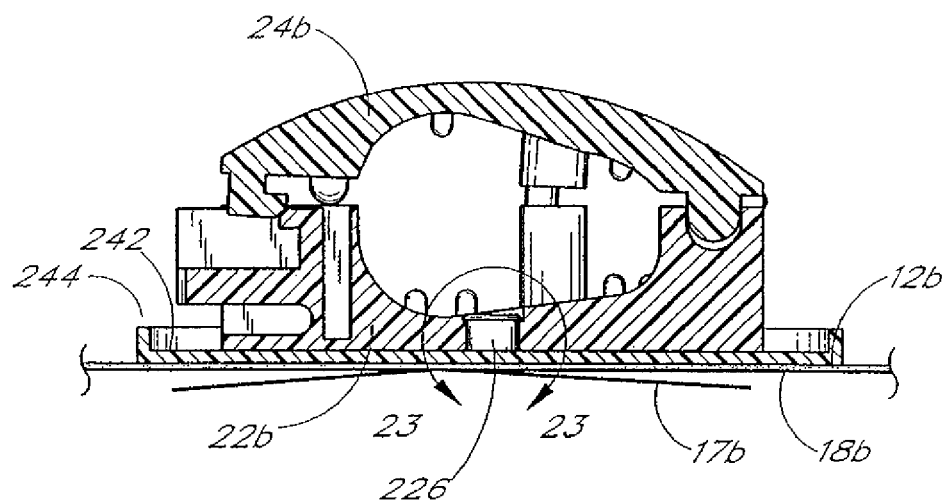
FIG. 22 is a cross-sectional view of the anchoring system of FIG. 21 taken along line 22-22.
Figure 23:
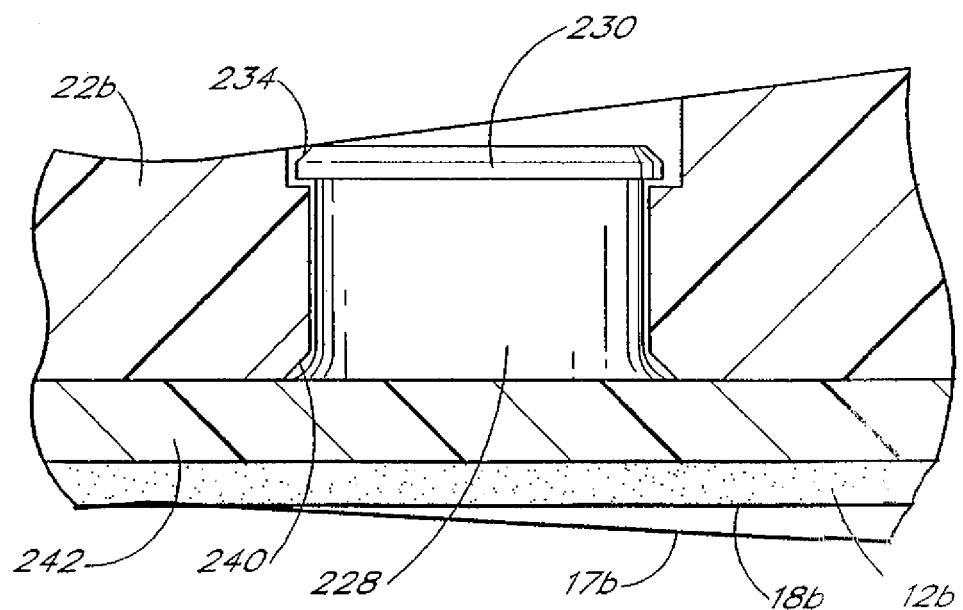
FIG. 23 is an enlarged detail view of a cross-sectional view of a rotatable mount of FIG. 22 circumscribed by line 23-23.

An anchoring system in accordance with another embodiment of the invention is illustrated in FIGS. 21-23. The principal difference between this embodiment and the previous embodiments is that the retainer is rotatably mounted onto the anchor pad. For this purpose, like reference numerals with a "b" suffix have been used to indicate like components between the embodiments with the understanding that the above description of such common components applies equally to the embodiment shown in FIGS. 21-24, unless indicated otherwise. In this regard, it should be appreciated that the general construction of the retainer is in accordance with the description provided in connection with the embodiments illustrated in FIGS. 1-13; however, the latch mechanism of the retainer is in accordance with the description provided in connection with the embodiment illustrated in FIGS. 14-20.

The principles of the present embodiment that provide an anchoring system 10b for securing a catheter are similar to the principles of the previous embodiments. The present embodiment, however, includes an additional feature that allows the retainer 20b to be rotated by at least some degree, and preferably by 360°, relative to the anchor pad 12b, as described below. For this purpose, in the illustrated embodiment, a mounting post 226 is attached to the anchor pad 12b and a hole 232 is formed in the base 22b of the retainer 20b.

As best seen in FIGS. 21-23, the mounting post 226 is attached to the anchor pad 12b and the through-hole 232 is formed in the base 22b of the retainer 20b. The mounting post 226 and through-hole 232 allow the retainer 20b to pivot relative to the anchor pad 12b. In the illustrated embodiment, the retainer 20b can be rotated 360° relative to a central pivot point fixed to the anchor pad 12b; however, the degree of rotation also can be confined.

Relative rotation is advantageous to assist the healthcare provider in attaching and detaching the retainer 20b to the catheter (not shown). Relative rotation is also advantageous to assist the healthcare provider in adjusting the attached catheter-retainer assemblage so that the catheter is less likely to become kinked or snagged on an object. Relative rotation is further advantageous to assist in positioning the catheter in-line with the drainage lumen or other object. In addition, the healthcare provider need not precisely align the retainer relative to an axis of the catheter before attaching the pad to the patient's skin. The healthcare provider can coarsely align the anchoring system on the patient, adhere the pad to the patient's skin and then rotate the retainer to align the channel of the base with the axis of the catheter. The rotatable nature of the retainer thus eases connection and disconnection of the catheter with the retainer.

Figure 24:
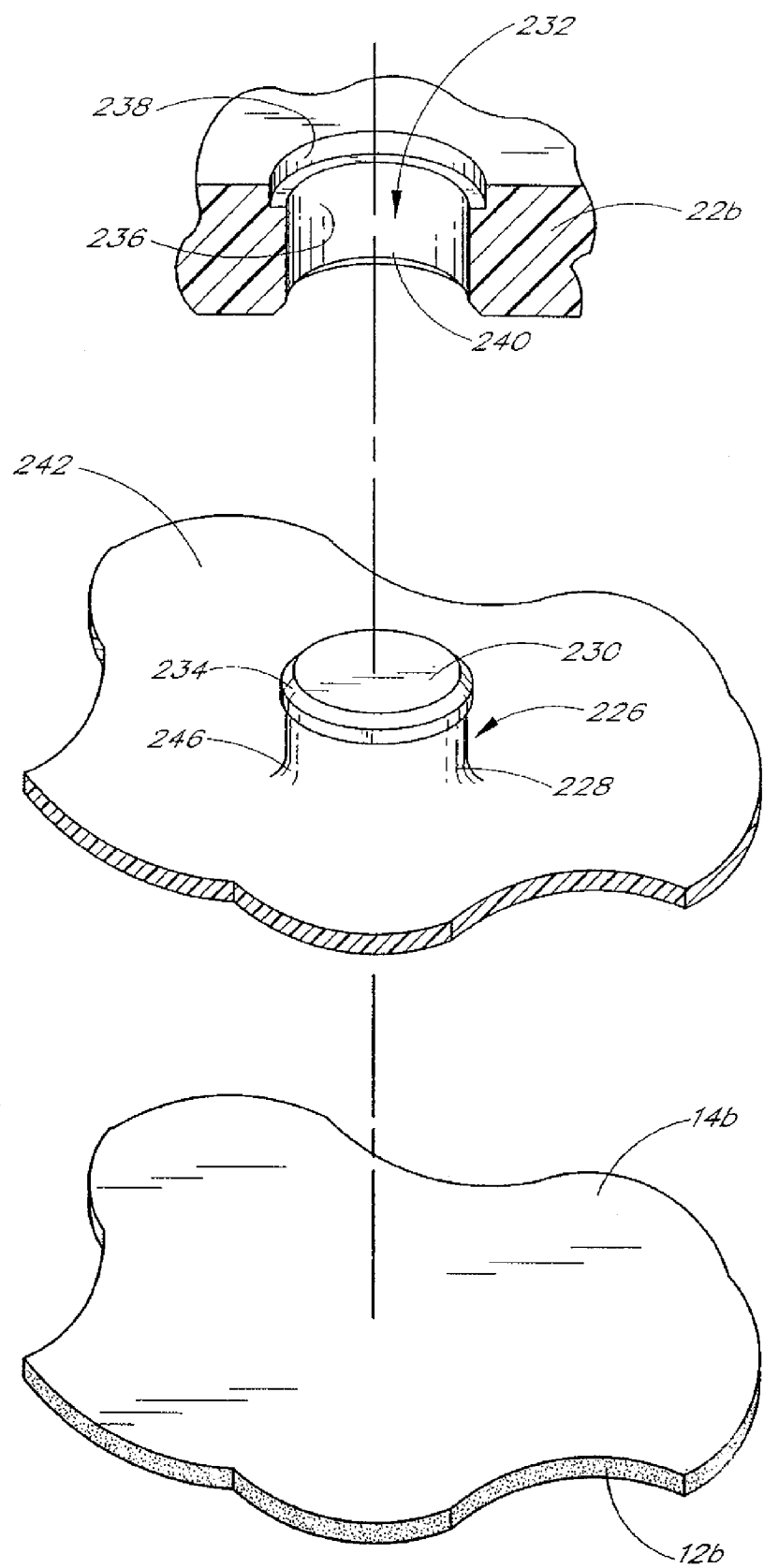
FIG. 24 is an enlarged, exploded detail view of a rotatable mount and a through-hole in the retainer of FIG. 23.

As best seen in FIGS. 23 and 24, the illustrated mounting post 226 comprises a pedestal 228 and a cap 230 configured for acceptance into a through-hole 232 formed in the base 22b of the retainer 20b. The pedestal 228 is attached to and extends upwardly from the anchor pad 12b. The pedestal 228 can have a variety of transverse heights, depending upon the particular application and the particular retainer to which it interacts. For anchoring Foley catheters and for use with the retainer described in FIGS. 1 and 14, the pedestal 228 desirably has a transverse height slightly small than that of the base 22b at the location of the hole 232; that is, the height can be about 1-5 mm, and more particularly about 2 mm; however, other heights are also possible. The illustrated pedestal 228 has a generally cylindrical shape, but can be configured in a variety of other shapes, which can match the shape of the hole 232 in the retainer base 22b. The diameter of the pedestal 228 is sufficient to perform its structural function of coupling the anchor pad 12b to the base 22b without significantly bending or breaking and desirably has a diameter of about 1 to 5 mm and more particularly a diameter of about 4 mm; however, larger or smaller diameters are also possible. Thus, the diameter of the pedestal 228 is desirably about twice the height of the pedestal 228. The pedestal 228 is flared at the bottom to form an annular fillet 246. The fillet 246 provides structural strength to the pedestal 226 to resist shear and other forces that can otherwise cause the pedestal to break off from the mounting base 242 or otherwise fail.

The cap 230 extends radially outward from the top portion of the pedestal 228. The cap 230 assists in coupling the anchor pad 12b to the base 22b by inhibiting separation of the pedestal 228 from the base 22b, as explained below. The radial diameter of the cap 230 can vary, depending upon the particular application, and desirably is about 1-5 mm, and more particularly a diameter of about 2 mm; however, larger or smaller diameters are also possible. The illustrated cap 230 has a cross sectional shape generally similar to that of the pedestal 228 for ease of manufacture, however, it can be configured in a variety of other cross sectional shapes to generally match the shape of the through-hole 232 in the base, which is described below. The cap 230 desirably extends beyond the circumference of the pedestal 228 to assist in securely coupling the anchor pad 12b to the retainer 20b, however, the cap 230 need not circumscribe the entire pedestal 228 and can comprise only a single radial member that extends outwardly from the pedestal 228. The transverse thickness of the cap 230 is sufficient to perform its structural function of coupling the anchor pad 12a to the retainer 20b without significantly bending or breaking and desirably has a thickness of about 0.5 to 2 mm and more particularly a thickness of about 1 mm; however, larger or smaller thicknesses are also possible. A chamfer 234 can be formed on an upper peripheral edge of the cap 230 to assist in the assembly of the mounting post 226, as described below. The illustrated chamfer 234 transversely extends for about one-half the thickness of the cap 230.

The mounting post pedestal 228 desirably have a smooth side surfaces to facilitate sliding of the retainer 20b relative to the mounting post 226, such that the mounting posts 226 provide a bearing surface for the retainer base 22b. The top of the cap 230 additionally is smooth and planar to present a surface that is generally flush with the surface of the base 22b within the channel. It is understood, however, that the curvilinear configuration of the channel surface of the base 22b, results in an imperfectly flush surface between the base and the cap 230, although the top of the cap 230 could be configured to match the curvilinear configuration of the surface of the base 22b and thereby present a perfectly flush surface. The mounting post 226 has a one-piece unitary configuration for ease of manufacture and strength; however, the mounting post 226 can alternatively comprise a plurality of separate components that attach to form the mounting post 226. Although the illustrated mounting post 226 is generally mushroom shaped with a generally flat top, the mounting post 226 can also be generally T-shaped, inversely L-shaped and the like.

The mounting post 226 is desirably formed in unity with a mounting base 242 for structural strength; however, the mounting post 226 and the mounting base 242 can comprise separate components, as noted below. The mounting base 242 provides a larger footprint, relative to that of the mounting post 226, so that the mounting post 226 can be more securely attached to the anchor pad 12b and inhibit unintended separation of the mounting post 226 from the anchor pad 12b. For example, if the anchoring system 10b is adhered to the inner thigh of a bedridden patient, movement of the patient can generate forces on the anchoring system 10b. Thus, the larger footprint which the mounting base 242 provides, and which the mounting post 226 is preferably in unity with, provides increased securement between the mounting post 226 and anchor pad 12b and enhances the robustness of the anchoring system.

The mounting base 242 is generally planar to match the upper surface 14b of the anchor pad 12b. The illustrated plate also has a circular configuration, with the mounting post 226 located at the center of the plate so that the retainer 20b can centrally rotate on the mounting base 242; however, the base can have other shapes as well.

An upturned lip 242 desirably circumscribes the perimeter of the mounting base 242 to form a barrier that inhibits inwardly directed radial forces from shearing or otherwise separating the retainer 20b or mounting post 226 from the mounting base 242. The illustrated lip 244 has a transverse height of about 1-5 mm for this purpose. The lip 244 diameter is slightly larger than the lateral width of the retainer 20b (i.e., larger by about 1 mm); however, the lip 244 can alternatively be arranged to radially abut the retainer 20b when the retainer 20b rotates on the mounting base 242, or to provide a radial clearance between the retainer 20b and the lip 244. When so configured, the lip does not interfere with the interengaging structure (i.e., does not extend transversely above the latching mechanism so as to inhibit the medical attendant's fingers from depressing the latching mechanism, or abut the retainer so as to partially depress the latching mechanism when the retainer is rotated). The lip 244 additionally does not extend above the bottom of the channel 60 and thus do not present an edge about which the catheter could kink. In the illustrated embodiment, the lip 244 is shorter than the mounting post 226. The lip also does not interfere with the free rotation of the retainer; however, the mounting base 242 and the retainer 20b can include cooperating structure which establishes incremental angular positions of the retainer as it rotates over the mounting base 242. This can be done by providing a plurality of ratchet teeth about the inner side surface of the lip 244 and a cooperating tang formed on the retainer 20b. In this manner, the orientation of the retainer 20b on the mounting base 242 can be set until a sufficient force is applied to the retainer to overcome the engagement between the tang and the corresponding ratchet teeth.

In the illustrated embodiment, as best understood from FIGS. 23 and 24, the base 22b of the retainer 20b has a through-hole 232 sized and configured to recover the post and more preferably to generally match that of the mounting post 226 so that the retainer 20b can rotate relative to the anchor pad 12b about the mounting post 226. The illustrated through-hole 232 extends through the base 22b and has a first or lower diameter 236 and a second or upper diameter 238. The lower diameter 236 is slightly larger than that of the pedestal 228 and the upper diameter 238 is slightly larger than that of the cap 230. The tolerance between the through-hole 232 and the mounting post 226 desirably is about 0.1-0.5 mm and more particularly about 0.1-0.2 mm. Like the mounting post 226, the through-hole 232 has a smooth surface to minimize function when the retainer is rotated. A chamfer 240 can circumscribe the lower portion of the lower diameter 236 to assist in the assembly of the rotatable mounting post 226, as described below.

When assembled, the mounting post 226 is arranged within the through-hole 232 and secured to the anchor pad 12b. In particular, the top of the cap 230 is generally flush with the top of the base 22b, the cap 230 is housed within the upper diameter 238, the pedestal 228 is housed within the lower diameter 236, and the bottom of the pedestal 228 is secured to the anchor pad 12b. The mounting base 242 is desirably secured to the upper surface 14b of the anchor pad 12b by a solvent bond adhesive, such as cyanoacylate or other bonding material. One such adhesive is available commercially as Part No. 4693 from the Minnesota Mining and Manufacturing Company (3M). One suitable assembly process, advantageously used when the mounting post 226 and mounting base 242 are in formed in unity, involves bonding the bottom of the mounting base 242 to the upper surface 14b of the anchor pad 12b and then urging the cap 230 of the mounting post 226 through the through-hole 232. The chamfer 240 that circumscribes the through-hole 232 and the chamfer 234 that circumscribes the cap 230 cooperate to allow the cap 230 to deform and advance through the through-hole 232. Another suitable assembly process, advantageously used when the mounting post 226 and mounting base 242 comprise separate components, involves placing the pedestal 228 through the through-hole 232 such that the pedestal 228 extends through the first diameter 236 while the cap 230 catches on the second diameter 238, then bonding the bottom of the pedestal 228 to the mounting base 242, and then bonding the mounting base 242 to the anchor pad 12b. By this configuration, the retainer 20b can rotate 360° relative to the anchor pad 12b.

Although this invention has been described in terms of a certain preferred embodiment and suggested possible modifications thereto, other embodiments and modifications apparent to those of ordinary skill in the art are also within the scope of this invention. Accordingly, the scope of the invention is intended to be defined only by the claims which follow.

What is claimed is:

1. An anchoring system for securing a medical article having at least one Y-site to the body of a patient, comprising:
   an anchor having an upper surface and a lower surface, at least a portion of the lower surface having an adhesive surface to attach the anchor to the body of the patient; and
   a retainer supported by the anchor, said retainer being capable of receiving a portion of the medical article, the retainer including a base, a cover, and a post, said base being disposed on the upper surface of the anchor, said cover being movably connected to the base so as to move between an open position and a closed position, the cover lying above at least part of the base when in the closed position, and the post being arranged on said retainer so as to at least partially lie between said cover and said base when the cover is in the closed position and fall within the Y-site at least when the medical article is placed within the retainer and the cover is in the closed position, the post connecting the base to the cover and having a first portion and a second portion, a distal end of the first portion overlapping a distal end of the second portion along a transverse axis when the cover is in the closed position so as to inhibit movement of the medical article through the post, and the post having a longitudinal length less than a longitudinal length of the cover.

2. An anchoring system as in claim 1, wherein the base and cover cooperate to form a receiving space when the cover lies in the closed position, the receiving space configured to receive at least a portion of the medical article.

3. The anchoring system as in claim 1, wherein the base defines a receiving space on the retainer, and the cover is arranged on the base so as to cover at least a portion of the receiving space when in the closed position.

4. The anchoring system as in claim 3, wherein a width of the receiving space tapers over its length.

5. An anchoring system as in claim 3 further comprising a protrusion disposed on a portion of the receiving space, the protrusion impinging on a portion of the medical article at least when the cover is in the closed position.

6. The anchoring system as in claim 3, wherein the cover lies generally to at least one side of the base in the open position to thereby expose the receiving space.

7. The anchoring system as in claim 3, wherein the post is disposed within the receiving space.

8. The anchoring system as in claim 3 further comprising a latching mechanism operable between the base and the cover to releasably secure the cover to the base.

9. The anchoring system as in claim 8, wherein the receiving space is disposed at a position between the latching mechanism and a pivotal coupling between the cover and the base.

10. The anchoring system as in claim 1 further comprising at least one retention mechanism disposed within the receiving space and including at least first and second members, the first and second members being arranged to cooperate with one another when the cover is in the closed position so as to hold a portion of the medical article between the first and second members without substantially occluding an inner lumen of the medical article.

11. The anchoring system as in claim 1 further comprising means for inhibiting movement of the retained portion of the medical article through the receiving space of the retainer.

12. The anchoring system as in claim 1 further comprising at least one projection and at least one cooperating recess, the projection extending from one of the cover and the base and the recess receding into the other one of the cover and the base, at least a portion of the projection configured to fit within the recess.

13. An anchoring system as in claim 12, wherein the projection has a length that is greater than a depth of the recess.

14. The anchoring system as in claim 1, wherein the retainer is rotatably attached to the anchor.

15. An anchoring system for securing an elongated medical article having at least one branching site to the skin of a patient, comprising:
 an anchor having an upper surface and a lower surface, at least a portion of the lower surface formed with an adhesive layer;
 a retainer rotatably attached to the upper surface of the anchor, and comprising a base, post, and a cover pivotally coupled to the base and moveable between an open position and a closed position, the cover and the base cooperating to define at least one channel when the cover lies in the closed position, the channel being configured to receive at least a portion of the elongated medical article, and the post being arranged on said retainer so as to at least partially lie between said cover and said base when the cover is in the closed position and fall within the branching site at least when the medical article is placed within the retainer and the cover is in the closed position, the post connecting the base to the cover and having a first portion and a second portion, a distal end of the first portion overlapping a distal end of the second portion along a transverse axis when the cover is in the closed position so as to inhibit movement of the medical article through the post, and the post having a longitudinal length less than a longitudinal length of the cover; and
 at least one retainer member projecting into the channel and arranged to be capable of engaging a portion of the medical article.

16. The anchoring system as in claim 15, wherein at least a portion of the channel includes a width, as measured in a lateral direction, which tapers in size.

17. The anchoring system as in claim 15 further comprising a latching mechanism operable between the base and the cover to secure the cover to the base when the cover is in the closed position.

18. The anchoring system as in claim 15 further comprising a mounting base fixed relative to the anchor, and a rotatable coupling connecting the mounting base to the base of the retainer.

19. An anchoring system as in claim 18, wherein the rotatable coupling is formed by a post affixed to the mounting base and a receptacle formed in the base of the retainer, the receptacle receiving at least a portion of the post.

20. An anchoring system for securing an elongated medical article having at least one Y-site to a patient, comprising:
 an anchor having an upper surface and a lower surface; and
 a retainer mounted on the upper surface of the anchor and capable of receiving a portion of the medical article, the retainer including:
  a base having first and second sides and a first portion of a post;
  a cover having a first side and a second side and a second portion of the post, the first side of the cover being coupled to the first side of the base, and the second side of the cover being movable between a closed position, in which the second side of the cover lies generally above the second side of the base, and an open position, in which the second side of the cover is spaced apart from the second side of the base so as to expose the base, the base and cover defining a receiving space when the cover lies in the closed position, wherein at least a portion of the post lies between the first and second sides of the base and within the Y-site at least when the medical article is placed within the retainer and the cover is in the closed position, a distal end of the first portion of the post overlapping a distal end of the second portion of the post along a transverse axis when the cover is in the closed position so as to inhibit movement of the medical article through the post, and the post having a longitudinal length less than a longitudinal length of the cover; and
  a latching mechanism operable between the base and the cover to releasably secure the second side of the cover to the second side of the base.

21. The anchoring system as in claim 20, wherein the receiving space includes a proximal end and a distal end, and the width of the receiving space, as measured in a lateral direction, is smaller at the proximal end of the receiving space than at the distal end of the receiving space.

22. The anchoring system as in claim 20, wherein the latching mechanism is disposed separately from the post.

23. An anchoring system for securing an elongated medical article to a patient, comprising:
   an anchor having an upper surface and a lower surface, the lower surface including an adhesive layer on at least a portion of the surface; and
   a retainer mounted on the upper surface of the anchor and capable of receiving a portion of the medical article, the retainer including:
      a base having first and second sides, and a first groove with a generally curvilinear cross-sectional shape,
      a cover having a first side and a second side, the first side of the cover being attached to the first side of the base, and the second side of the cover being moveable between a closed position, in which the second side of the cover lies generally above the second side of the base, and an open position, in which the second side of the cover is spaced apart from the second side of the base so as to expose the groove in the base, the cover including a second groove having a generally curvilinear cross-sectional shape generally corresponding in position to the first groove in the base to define a channel when the cover lies in the closed position, the defined channel having a curvilinear cross-sectional shape with a cross-sectional area of the channel varying along the length of the channel, and
      a post connecting the base to the cover and having a first portion and a second portion, a distal end of the first portion overlapping a distal end of the second portion along a transverse axis when the cover is in the closed position so as to inhibit movement of the medical article through the post, the post having a longitudinal length less than a longitudinal length of the cover.

24. An anchoring system for securing an elongated medical article, comprising:
   an anchor having an upper surface and a lower surface, at least a portion of the lower surface being formed with an adhesive layer; and
   a retainer permanently affixed to the upper surface of the anchor, and comprising:
      a base having a first generally curvilinear groove to receive at least a portion of the elongated medical article,
      a cover being pivotally coupled to the base and moveable between an open position in which the groove is exposed, and a closed position in which the groove is covered, the cover including a second generally curvilinear groove that cooperates with the first groove when the cover is in the closed position to define a channel, the channel being configured to support the portion of the medical article received by the retainer on at least diametrically opposed sides thereof along the entire length of the received portion of the medical article, and
      a post connecting the base to the cover and having a first portion and a second portion, a distal end of the first portion overlapping a distal end of the second portion along a transverse axis when the cover is in the closed position so as to inhibit movement of the medical article through the post, the post having a longitudinal length less than a longitudinal length of the cover.

25. The anchoring system as in claim 24 further comprising at least one retention member projecting into the channel and arranged to be capable of engaging a portion of the medical article to inhibit longitudinal movement of the medical article through the channel.

* * * * *